(12) United States Patent
Elliman

(10) Patent No.: US 11,926,848 B2
(45) Date of Patent: *Mar. 12, 2024

(54) STROMAL STEM CELLS

(71) Applicant: Orbsen Therapeutics Limited, Galway (IE)

(72) Inventor: Stephen J. Elliman, Galway (IE)

(73) Assignee: Orbsen Therapeutics Limited, Galway (IE)

( * ) Notice: Subject to any disclaimer, the term of this patent is extended or adjusted under 35 U.S.C. 154(b) by 67 days.

This patent is subject to a terminal disclaimer.

(21) Appl. No.: 17/470,492

(22) Filed: Sep. 9, 2021

(65) Prior Publication Data

US 2022/0112466 A1 Apr. 14, 2022

Related U.S. Application Data

(60) Continuation of application No. 16/009,048, filed on Jun. 14, 2018, now Pat. No. 11,142,747, which is a division of application No. 15/089,435, filed on Apr. 1, 2016, now Pat. No. 10,907,131, which is a division of application No. 14/377,597, filed as application No. PCT/EP2013/052692 on Feb. 11, 2013, now Pat. No. 11,230,700.

(30) Foreign Application Priority Data

Feb. 10, 2012 (GB) .................................. 1202319

(51) Int. Cl.
| | |
|---|---|
| *C12N 5/0775* | (2010.01) |
| *A61K 9/00* | (2006.01) |
| *A61K 35/28* | (2015.01) |
| *A61K 35/407* | (2015.01) |
| *C12N 5/074* | (2010.01) |
| *C12N 5/077* | (2010.01) |
| *C12Q 1/37* | (2006.01) |
| *G01N 33/50* | (2006.01) |

(52) U.S. Cl.
CPC .......... *C12N 5/0662* (2013.01); *A61K 9/0019* (2013.01); *A61K 35/28* (2013.01); *A61K 35/407* (2013.01); *C12N 5/0607* (2013.01); *C12N 5/0663* (2013.01); *C12N 5/0669* (2013.01); *C12Q 1/37* (2013.01); *G01N 33/5005* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,726,058 A | 3/1998 | Jalkanen et al. | |
| 6,355,239 B1 | 3/2002 | Bruder et al. | |
| 6,531,295 B1 | 3/2003 | Saunders et al. | |
| 10,124,038 B2 | 11/2018 | Elliman | |
| 10,251,934 B2 | 4/2019 | Elliman | |
| 10,907,131 B2 | 2/2021 | Elliman | |
| 10,920,197 B2 | 2/2021 | Elliman | |
| 11,026,994 B2 | 6/2021 | Elliman | |
| 11,142,747 B2 | 10/2021 | Elliman | |
| 11,434,471 B2 | 9/2022 | Elliman | |
| 2003/0225018 A1 | 12/2003 | Ekker et al. | |
| 2004/0258670 A1 | 12/2004 | Laughlin et al. | |
| 2005/0059147 A1 | 3/2005 | Seshi | |
| 2005/0226864 A1 | 10/2005 | Hinton et al. | |
| 2006/0078993 A1 | 4/2006 | Phan et al. | |
| 2007/0264239 A1 | 11/2007 | Huard et al. | |
| 2008/0241246 A1 | 10/2008 | Sakthivel et al. | |
| 2010/0172885 A1 | 7/2010 | Pittenger et al. | |
| 2010/0196329 A1 | 8/2010 | Ra et al. | |
| 2010/0247577 A1 | 9/2010 | Foussat et al. | |
| 2012/0207725 A1 | 8/2012 | Cho et al. | |
| 2014/0356398 A1 | 12/2014 | Riddell et al. | |
| 2015/0030615 A1 | 1/2015 | Derr et al. | |
| 2015/0037292 A1 | 2/2015 | Ellman | |
| 2016/0058832 A1 | 3/2016 | Elliman | |
| 2016/0215265 A1 | 7/2016 | Elliman | |
| 2016/0271211 A1 | 9/2016 | Elliman et al. | |
| 2016/0361364 A1 | 12/2016 | Corbascio et al. | |
| 2018/0298341 A1 | 10/2018 | Elliman | |

(Continued)

FOREIGN PATENT DOCUMENTS

| | | |
|---|---|---|
| CN | 1678734 A | 10/2005 |
| EP | 1795588 A1 | 6/2007 |

(Continued)

OTHER PUBLICATIONS (Abstract C34.6) Abstracts of papers presented at Glyco XVI, XVI International Symposium on Glycoconjugates, Aug. 19-24, 2001, The Hague, The Netherlands, Glycoconjugate Journal, 18(1-2): 1-202, 2001.
Alvarez-Viejo, Maria: CD271 as a marker to identify mesenchymal stem cells from diverse sources before culture. World Journal of Stem Cells. vol. 7, No. 2, Jan. 1, 2015, p. 470.
AU2014255755 Office Action dated Sep. 7, 2018.
Australian Patent Application No. 2013217870 Examination Report dated Apr. 24, 2018.
Australian Patent Application No. 2013217870 Examination Report No. 1 dated Nov. 1, 2017.
Australian Patent Application No. 2014255755 Examination Report No. 1 dated Oct. 10, 2017.

(Continued)

*Primary Examiner* — Teresa E Knight
(74) *Attorney, Agent, or Firm* — Wilson Sonsini Goodrich & Rosati

(57) ABSTRACT

Stromal stem cells are prospectively isolated from human bone marrow then expanded into clonal populations and cultured and used, the isolation being on the basis of expression of a cell surface marker, wherein the cell surface marker binds an antibody and wherein said antibody cross reacts with a cell surface marker found on mouse stromal stem cells or rat stromal stem cells, and optionally also on a cell of at least one other mammalian species selected from mouse, rat, horse, rabbit and pig cells. Useful stromal stem cell populations are positive for SDC2.

11 Claims, 11 Drawing Sheets

(56) References Cited

U.S. PATENT DOCUMENTS

| | | |
|---|---|---|
| 2019/0015331 A1 | 1/2019 | Elliman et al. |
| 2020/0149012 A1 | 5/2020 | Elliman et al. |
| 2020/0149110 A1 | 5/2020 | Targan et al. |
| 2020/0158725 A1 | 5/2020 | Singh et al. |
| 2021/0154235 A1 | 5/2021 | Couture et al. |
| 2022/0228122 A1 | 7/2022 | Elliman et al. |
| 2022/0288129 A1 | 9/2022 | Elliman et al. |

FOREIGN PATENT DOCUMENTS

| | | |
|---|---|---|
| EP | 2545928 A1 | 1/2013 |
| EP | 3271396 A1 | 1/2018 |
| EP | 3416964 A4 | 9/2019 |
| JP | 2013508353 A | 3/2013 |
| JP | 2016516797 A | 6/2016 |
| JP | 2017532965 A | 11/2017 |
| KR | 20080075959 A | 8/2008 |
| KR | 20100106744 A | 10/2010 |
| KR | 20120013915 A | 2/2012 |
| KR | 101309910 B1 | 9/2013 |
| WO | WO-9734605 A1 | 9/1997 |
| WO | WO-9961587 A1 | 12/1999 |
| WO | WO-0180865 A2 | 11/2001 |
| WO | WO-02087609 A1 | 11/2002 |
| WO | WO-03046141 A2 | 6/2003 |
| WO | WO-03062386 A2 | 7/2003 |
| WO | WO-2004003179 A1 | 1/2004 |
| WO | WO-2007122823 A1 | 11/2007 |
| WO | WO-2008100083 A1 | 8/2008 |
| WO | WO-2009012357 A2 | 1/2009 |
| WO | WO-2009105624 A2 | 8/2009 |
| WO | WO-2010065239 A1 | 6/2010 |
| WO | WO-2010119039 A1 | 10/2010 |
| WO | WO-2011153458 A2 | 12/2011 |
| WO | WO-2011160055 A2 | 12/2011 |
| WO | WO-2012111997 A2 | 8/2012 |
| WO | WO-2012125471 A1 | 9/2012 |
| WO | WO-2013117761 A1 | 8/2013 |
| WO | WO-2013172793 A1 | 11/2013 |
| WO | WO-2014168548 A2 | 10/2014 |
| WO | WO-2014170411 A1 | 10/2014 |
| WO | WO-2015038075 A1 | 3/2015 |
| WO | WO-2016026854 A2 | 2/2016 |
| WO | WO-2016154019 A1 | 9/2016 |
| WO | WO-2017122095 A1 | 7/2017 |
| WO | WO-2018220442 A2 | 12/2018 |
| WO | WO-2019012334 A2 | 1/2019 |
| WO | WO-2020035741 A2 | 2/2020 |
| WO | WO-2021038289 A1 | 3/2021 |

OTHER PUBLICATIONS

Australian Patent Application No. 2014255755 Examination Report No. 2 dated Jun. 27, 2018.
Bermadez-Lugo et al.: Exploration of the valproic acid binding site on histone deacetylase 8 using docking and molecular dynamic simulations. Journal of Molecular Modeling, 18(6):2301-2310, 2011.
British Society for Matrix Biology-Spring 2012 Meeting Report. International Journal of Experimental Pathology, 94:A1-A48, 2013.
Canadian Patent Application No. 2863821 Examination Report dated Nov. 6, 2018.
Canadian Patent Application No. 2863821 Examination Report dated Jun. 2, 2021.
Carlotti, Francoise, et al.: Isolated human islets contain a distinct population of mesenchymal stem cells, Islets, p. 164-173 May/Jun. 2010.
Chinese Application No. 2014800251845 Office Action dated May 31, 2021.
Chinese Patent Application No. 201380019351.0 Second Office Action dated Jun. 10, 2016.
Chinese Patent Application No. 201380019351.0 Third Office Action dated Jan. 12, 2017.
Christianson and Belting. Heparan sulfate proteoglycan as a cell-surface endocytosis receptor. Matrix Biology, 35:51-55, 2014.
Chung et al.: Human Embryonic Stem Cell Lines Generated without Embryo Destruction. Cell Stem Cell, vol. 2, No. 2, 2008, pp. 113-117.
CN201480025184.5 Office Action dated Jul. 4, 2018.
Costabel et al.: Pirfenidone in idiopathic pulmonary fibrosis: Expert panel discussion on the management of drug-related adverse events. Adv. Ther., 31:375-391, 2014.
Cuthbert et al.: Single-platform quality control assay to quantify multipotential stromal cells in bone marrow aspirates prior to bulk manufacture or direct therapeutic use. CYTOTHERAPY, 2012, vol. 14, No. 4, pp. 431-440.
Database: NCBI Reference Sequence: NP_002989.1 (2 pgs.) (Jan. 20, 2003).
Davey et al.: Mesenchymal stem cell-based treatment for microvascular and secondary complications of diabetes mellitus. Frontiers in Endocrinology 5:86 [1-16]. doi: 10.3389/fendo.2014.00086 (2014).
Dieudonne et al. Targeted inhibition of T-cell factor activity promotes syndecan-2 expression and sensitization to doxorubicin in osteosarcoma cells and bone tumors in mice. J Bone Miner Res 27(10):2118-2129 (2012).
Dieudonne et al. High Wnt signaling represses the proapoptotic proteoglycan syndecan-2 in osteosarcoma cells. Cancer Res 70(13):5399-5408 (2010).
Duffy et al.: Mesenchymal stem cell inhibition of T-helper 17 cell-differentiation is triggered by cell-cell contact and mediated by prostaglandin E2 via the EP4 receptor. European Journal of Immunol., 41:2840-2851, 2011.
Eskildsen et al.: MicroRNA-138 regulates osteogenic differentiation of human stromal (mesenchymal) stem cells in vivo. PNAS, 108(15):6139-6144, 2011.
Essner et al.: Syndecan-2. International Journal of Biochemistry and Cell Biology. 38(2):152-156, 2006.
European Patent Application No. 14718403.0 Communication dated Apr. 6, 2017.
European Patent Application No. 14718403.0 Communication dated Mar. 6, 2018.
European Patent Application No. 14718403.0 Examination Report dated Jan. 2, 2019.
European Patent Application No. 15158384.6 Communication dated Apr. 7, 2017.
European Patent Application No. 15158384.6 Extended European Search Report dated Jul. 8, 2015, 10 pages.
European Patent Application No. 16714673.7 Office Action dated Sep. 12, 2018.
European Patent Application No. 18190005.1 European Search Report dated May 3, 2019.
Final Report Summary—REDDSTAR (Repair of Diabetic Damage by Stromal Cell Administration). European Commission https://cordis.europa.eu/result/rcn/197094_en.html 1-28 (2017).
Final Report Summary—Core of Report—REDDSTAR (Repair of Diabetic Damage by Stromal Cell Administration). European Commission https://cordis.europa.eu/docs/results/305/305736/final1-reddstar-final-report-core-of-report.pdf 1-44 (2017).
Frantz et al. The extracellular matrix at a glance. Cell Science at a Glance 123, (2010), 4195-4200.
GB1202319.8 Search Report dated Jun. 11, 2012, 3 pages.
Gronthos et al. Molecular and cellular characterisation of highly purified stromal stem cells derived from human bone marrow. (2003) Journal of Cell Science, vol. 116:1827-1835.
Hagymasi et al.: Stem cell treatment in the treatment of gastrointestinal diseases. Orvosi Hetilap. 149(31):1449-1455 (2008).
Hayes et al.: Mesenchymal stem cells—a promising therapy for Acute Respiratory Distress Syndrome. F1000 Med Rep. 4:2:1-7 (2012).
Hohki et al.: Blockade of interleukin-6 signaling suppresses experimental autoimmune uveoretinitis by the inhibition of inflammatory Th17 responses. Experimental Eye Research, 91:162-170, 2010.
Horwitz et al.: Clarification of the nomenclature for MSC: The international society for cellular therapy position statement. Cytotherapy, 7:393-395, 2005.

(56) References Cited

OTHER PUBLICATIONS

Hsu et al. Neural stem cells, neural progenitors, and neurotrophic factors. Cell Transplant 16(2):133-150 (2007).
Huang et al.: Prognostic significance of altered expression of SDC2 and CYR61 in esophageal squamous cell carcinoma. Oncology Reports, 21:1123-1129, 2009.
Human/Mouse Integrin [alpha]11 Antibody. Jun. 30, 2015 (Jun. 30, 2015), 1 page, Retrieved from the Internet: URL:http://www.rndsystems.com/pdf/MAB4235.pdf.
Indian Patent Application No. 1777/KOLNP/2014 Office Action dated May 31, 2018.
International Patent Application No. PCT/IB2018/000687 International Search Report and Written Opinion dated Dec. 5, 2018.
International Patent Application No. PCT/IB2018/000939 International Search Report and Written Opinion dated Dec. 19, 2018.
Japanese Patent Application No. 2016-508166 Office Action dated Jun. 12, 2018.
Japanese Patent Application No. 2016-508166 Office Action dated Sep. 25, 2017.
Japanese Patent Application No. 2017-550240 Office Action dated Mar. 2, 2020.
Jones et al.: Large-Scale Extraction and Characterization of CD271+ Multipotential Stromal Cells From Bone in Health and Osteoarthritis, Arthritis & Rhuematism, vol. 62, No. 7, Jul. 2010, pp. 1944-1954.
Kaltz et al.: Novel markers of mesenchymal stem cells defined by genome-wide gene expression analysis of stromal cells from different sources. Experimental Cell Research, Academic Press, US, vol. 316, No. 16, (Oct. 1, 2010), pp. 2609-2617.
Keifer et al.: Inhibition of NF-êB Activity by Thalidomide through Suppression of IêB Kinase Activity, Journal of Biological Chemistry, American Society for Biochemistry and Molecular Biology, US, vol. 276, No. 25, Jun. 22, 2001, pp. 22382-22387.
Khan et al.: CD4+ T Cell-derived Novel Peptide Thp5 Induces Interleukin-4 Production in CD4+ T Cells to Direct T Helper 2 Cell Differentiation. J Biol Chem, 287, 2830-2835, 2011.
Kozanoglu, Ilknur, et al.: Human bone marrow mesenchymal cells express NG2: possible increase in discriminative ability of flow cytometry during mesenchymal stromal cell identification. Cytotherapy (2009) vol. 11, No. 5, pp. 527-533.
KR 10-2011-0078791 Abstract from STN CAPlus database.
KR 10-2013-09910.
KR1317507 Abstract from STN CAPlus database (1 pg) (2015).
Lambaerts et al.: The signalling mechanisms of syndecan heparen sulphate proteoglycans Current Opinion Cell Biol., 21(5):662-669 (2009).
Lim et al.: Cell surface heparan sulfate proteoglycans control adhesion and invasion of breast carcinoma cells Molecular Cancer, 14:15, 18 pages, 2015.
Lim et al.: Syndecan-2 regulation of morphology in breast carcinoma cells is dependent on RhoGTPases. Biochimica et Biophysica Acta, 1840:2482-2490, 2014.
Llinas, L, et al.: Expression profiles of novel cell surface molecules on B-cell subsets and plasma cells as analyzed flow cytometry, Immunology Letters, vol. 134, No. 2, Jan. 30, 2011, pp. 113-121.
Lotufo et al.: Expression of cell-surface heparan sulfate proteoglycans in human cyclosporin-induced gingival overgrowth. J.Periodont Res., 42:553-558, 2007.
Lyons and Parish. Determination of lymphocyte division by flow cytometry. Journal of Immunological Methods, 171:131-137, 1994.
Manon-Jensen et al.: Proteoglycans in health and disease: the multiple roles of syndecan shedding FEBS Journal, 277(19):3876-3889, 2010.
Matesanz-Isabel et al.: New B-cell CD molecules. Immunology Letters, 2011, vol. 134, No. 2, pp. 104-112.
Mendez-Ferrer et al.: Mesenchymal and haematopoietic stem cells form a unique bone marrow niche Nature, 466:829-836 (2010).
Mendez-Ferrer et al.: Mesenchymal and haematopoietic stem cells form a unique bone marrow niche Nature, 466:829-836 (2010) Supplementary Information, 21 pages.
Mukhopadhyay et al.: Syndecan-2 and Decorin: Proteoglycans With a Difference-Implications in Keloid Pathogenesis, Journal of Trauma Injury Infection and Critical Care, 68(4):999-1008, 2010.
Mytilinalou et al.: Research Communication: Syndecan-2 is a key regulator of transforming growth factor beta 2/Smad2-mediated adhesion in fibrosarcoma cells. IUBMB Life, 65(2):134-143 (2013).
Nauta et al.: Chapter 2, Humoral and Cellular Immunity, in: Statistics in Clinical Trials, Berlin: Springer-Verlag, p. 13-17, 2011.
Nierhoff et al. New cell surface markers for murine fetal hepatic stem cells identified through high density complementary DNA microarrays. Hepatology 46(2):535-547 (2007).
Nish et al.: T cell-intrinsic role of IL-6 signaling in primary and memory responses. Elife, 3:e01949, 21 page (2014).
Nombela-Arrieta et al.: The elusive nature and function of mesenchymal stem cells. Nature Rev Mol Cell Bio. 12:126-131 (2011).
Paris et al.: Opposing Roles of Syndecan-1 and Syndecan-2 in Polyethyleneimine-mediated Gene Delivery. J Biol Chem, 283:7697-7704, 2008.
Parish. Fluorescent dyes for lymphocyte migration and proliferation studies. Immunology and Cell Biology, 77:499-508, 1999.
Park et al.: Syndecan-2 mediates adhesion and proliferation of colon carcinoma cells. The Journal of Biological Chemistry, 277(33):29730-29736, 2002.
Patil et al.: Enhancement of wound healing with increased angiogenesis in a diabetic rabbit ulcer model by topical application of CD362+ human mesenchymal stem cells (Cyndacel-M) seeded in Excellagen scaffold. Tissue Engineering Part A, 21(Supp. 1):S90 XP05509717 (2015).
PCT Patent Application No. PCT/EP2016/056065 International Search Report and Written Opinion dated May 20, 2016.
PCT Patent Application No. PCT/US2016/023178 International Search Report and Written Opinion dated Jun. 13, 2016.
PCT/EP2013/052692 International Preliminary Report on Patentability under Chapter II completed Mar. 13, 2014.
PCT/EP2013/052692 International Search Report completed Jun. 10, 2013.
PCT/EP2013/052692 Written Opinion Report completed Jun. 10, 2013.
PCT/EP2014/057830 International Preliminary Report On Patentability dated Oct. 20, 2015.
PCT/EP2014/057830 International Search Report and Written Opinion dated Jul. 17, 2014.
PCT/IB2017/000091 International Preliminary Report on Patentability dated Jul. 26, 2018.
PCT/IB2018/000687 International Preliminary Report on Patentability dated Dec. 3, 2019.
PCT/IB2018/000687 International Search Report and Written Opinion dated May 12, 2018.
PCT/IB2020/000680 International Search Report and Written Opinion dated Jan. 15, 2021.
PCT/IB2020/000680 Invitation to Pay Additional Fees dated Nov. 18, 2020.
PCT/US2016/023178 International Preliminary Report on Patentability dated Sep. 26, 2017.
PCT/US2017/000091 International Search Report and Written Opinion dated May 12, 2017.
Pennock et al.: T cell response: naive to memory and everything in between. Adv. Physiol. Educ. 37:273-283 (2013).
Rovira-Clave et al.: Syndecan-2 can promote clearance of T-cell receptor/CD3 from the cell surface. Immunology, 137(3):214-225 (Nov. 2012):E-Pub: Oct. 2, 2012.
Rozemuller et al.: Prospective isolation of mesenchymal stem cells from multiple mammalian species using cross-reacting anti-human monoclonal antibodies. Stem Cells and Development, vol. 19, No. 12, Dec. 1, 2010, pp. 1911-1921.
Ruiz et al.: Syndecan-2 is a novel target of insulin-like growth factor binding protein-3 and is over-expressed in fibrosis. Plos One, 7(8):1-4, 2012.
Russian Patent Application No. 2014136711 Office Action dated Jun. 1, 2017.
Russian Patent Application No. 2014136711 Official Action dated Feb. 23, 2017.

(56) References Cited

OTHER PUBLICATIONS

Russian Patent Application No. 2015148769 Office Action dated Mar. 19, 2018.
Russian Publication No. 2014136711A published Mar. 27, 2016.
Sanz-Nogués et al.: Angiogenic assessment of ORBCEL TM, a novel stromal cell population for treating Critical Limb Ischaemia (CLI); Cytotherapy, vol. 19, S198 (2017).
Sattler et al.: Inhibition of T-Cell Proliferation by Murine Multipotent Mesenchymal Stromal Cells is Mediated by CD39 Expression and Adensoine Generation, Cell Transplantation, vol. 20, No. 8, Sep. 1, 2011, pp. 1221-1230.
Shi et al.: Syndecan-2 exerts antifibrotic effects by promoting caveolin-1-mediated transforming growth factor-β receptor I internalization and inhibiting transforming growth factor-β1 signaling. Am J Respir Crit Care Med, 188:831-841, 2013.
Si et al.: CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Silva et al. The Profile of Gene Expression of Human Marrow Mesenchymal Stem Cells (2003) Stem Cells: vol. 21: 661-669.
Stepp et al.: Syndecan-1 and its expanding list of contacts. Advances in Wound Care, 4(4):235-249, 2015.
Tang et al.: Calcitriol suppresses antiretinal autoimmunity through inhibitory effects on the Th17 effector response. The Journal of Immunology, 182:4624-4632, 2009.
Technical Data Sheet, Purified Mouse Anti-human CD271, Jun. 6, 2013, p. 1-2.
Teixe et al.: Corrigendum to Syndecan-2 and -4 expressed on activated primary human CD4+lymphocytes can regulate T cell activation. Molecular Immunology, 51:368, 2012.
Teixe et al.: Syndecan-2 and -4 expressed on activated primary human CD4+ lymphocytes can regulate T cell activation. Molecular Immunology, 45:2905-2919, 2008.
Theocharis et al.: Insights into the key roles of proteoglycans in breast cancer biology and translational medicine. Biochimica et Biophysica Acta, 1855:276-300, 2015.
Turashev et al. Condition, destruction and reconstruction of the pericellular carbohydrate membrane of the luminal vascular surface in atherogenesis, Cardiological bulletin 2(2):64-68 (2007) (English Abstract).
UNIPROT: P34741, XP002726498, 3 pages, printed Jun. 26, 2014, http://ibis.internal.epo.org/exam/dbfetch.jsp?id=UNIPROT*P34741.
U.S. Appl. No. 14/377,597 Final Office Action dated Jan. 14, 2019.
U.S. Appl. No. 14/377,597 Final Office Action dated Oct. 1, 2020.
U.S. Appl. No. 14/377,597 Office Action dated Apr. 7, 2016.
U.S. Appl. No. 14/377,597 Office Action dated Aug. 15, 2018.
U.S. Appl. No. 14/377,597 Office Action dated Feb. 20, 2020.
U.S. Appl. No. 14/377,597 Office Action dated Jan. 30, 2017.
U.S. Appl. No. 14/377,597 Office Action dated Jun. 30, 2021.
U.S. Appl. No. 14/377,597 Office Action dated May 12, 2017.
U.S. Appl. No. 14/377,597 Office Action dated Nov. 6, 2015.
U.S. Appl. No. 14/377,597 Office Action dated Oct. 7, 2019.
U.S. Appl. No. 14/377,597 Office Action dated Sep. 9, 2016.
U.S. Appl. No. 14/785,001 Final Office Action dated Jun. 27, 2018.
U.S. Appl. No. 14/785,001 Office Action dated Dec. 15, 2017.
U.S. Appl. No. 14/785,001 Office Action dated Feb. 15, 2017.
U.S. Appl. No. 14/785,001 Office Action dated Jun. 20, 2016.
U.S. Appl. No. 15/074,681 First Action Interview Pilot Program Pre-Interview Communication dated Dec. 9, 2016.
U.S. Appl. No. 15/074,681 Office Action dated Apr. 27, 2017.
U.S. Appl. No. 15/074,681 Office Action dated Nov. 2, 2017.
U.S. Appl. No. 15/074,681 Restriction Requirement dated Aug. 22, 2016.
U.S. Appl. No. 15/089,435 Final Office Action dated Sep. 3, 2019.
U.S. Appl. No. 15/089,435 Non-Final Office Action dated Nov. 14, 2018.
U.S. Appl. No. 15/089,435 Office Action dated Jun. 10, 2020.
U.S. Appl. No. 15/089,435 Office Action dated Oct. 4, 2017.
U.S. Appl. No. 16/009,048 Final Office Action dated Jul. 24, 2020.
U.S. Appl. No. 16/009,048 Office Action dated Dec. 13, 2019.
U.S. Appl. No. 16/009,048 Restriction Requirement dated Jun. 28, 2019.
U.S. Appl. No. 16/070,202 Final Office Action dated Jul. 14, 2021.
U.S. Appl. No. 16/254,378 Final Office Action dated Oct. 15, 2020.
U.S. Appl. No. 16/254,378 Office Action dated Apr. 16, 2020.
U.S. Appl. No. 16/562,206 Final Office Action dated Nov. 27, 2020.
U.S. Appl. No. 16/562,206 Office Action dated Dec. 12, 2019.
U.S. Appl. No. 16/562,206 Office Action dated May 11, 2020.
U.S. Appl. No. 16/630,791 Office Action dated Jun. 25, 2021.
Wieczorek et al.: Gene expression profile of mouse bone marrow stromal cells determined by cDNA microarray analysis.Cell Tissue Res. 311(2):227-237 (2003).
Xian et al.: Syndecans as receptors and organizers of the extracellular matrix. Cell Tissue Res. 339:31-46 (2010).
Yan, Xin-Long, et al.: Migration of Dorsal Aorta Mesenchymal Stem Cells Induced by Mouse Embryonic Circulation, Dynamics 240: 65-74 (2011).
PCT/IB2020/000680 International Preliminary Report on Patentability dated Mar. 3, 2022.
U.S. Appl. No. 16/614,278 Final Office Action dated Aug. 17, 2022.
U.S. Appl. No. 16/614,278 Final Office Action dated Mar. 9, 2023.
U.S. Appl. No. 16/614,278 Office Action dated Apr. 20, 2022.
U.S. Appl. No. 16/614,278 Restriction Requirement dated Jan. 19, 2022.
U.S. Appl. No. 17/540,067 Office Action dated Feb. 24, 2022.

STROMAL STEM CELLS

CROSS-REFERENCE

This application is a continuation of Ser. No. 16/009,048, filed Jun. 14, 2018, which is a divisional of U.S. application Ser. No. 15/089,435 filed Apr. 1, 2016, issued as U.S. Pat. No. 10,907,131 on Feb. 2, 2021, which claims priority to U.S. application Ser. No. 14/377,597, a Section 371 U.S. national stage entry of pending International Patent Application No. PCT/EP2013/052692, international filing date Feb. 11, 2013, which claims priority to GB1202319.8, filed Feb. 10, 2012.

INTRODUCTION

The present invention relates to methods of isolating stem cells, to stem cell populations obtained from the isolated cells and to uses of those populations and of cells and tissue derived therefrom.

BACKGROUND

In the 1960s-70s, Friedenstein and colleagues demonstrated that osteogenic potential—revealed by heterotopic transplantation of bone marrow (BM) cells—was associated with a minor subpopulation of BM-mononuclear cells (MNCs) (reviewed in Friedenstein, 1990). These MNCs were distinguishable from the majority of hematopoietic MNC by their rapid adherence to plastic tissue culture vessels and by the fibroblast-like appearance of their progeny in culture, suggesting an origin from the stromal compartment of BM. As well as establishing BM stroma as the source, Friedenstein, Owen and colleagues provided a second breakthrough by showing that seeding of BM cell suspensions at clonal density results in the establishment of discrete colonies initiated by single cells (colony-forming unit fibroblastic, CFU-F [Friedenstein et al., 1970]).

Friedenstein and Owen later called this CFU-F generating cell the Stromal Stem Cell (SSC) (Owen and Friedenstein, 1988) and references to SSC herein are based on that original cell definition.

BM-derived SSCs can be identified in a mixed population of plastic-adherent (PA), fibroblastic, MNCs that give rise to bone, fat or cartilage and secrete potent immunomodulatory and angiogenic proteins. Preclinical studies demonstrate that PA-SSC mediate potent immunomodulatory and angiopoietic responses in vivo. Currently, clinical trials are testing PA-SSC in 40 distinct degenerative, autoimmune and ischemic diseases.

In the human marrow, approximately 1 BM mononuclear cell (MNC) in every 80,000 MNC is a CFU-F forming SSC. To date, the most simple and frequently used method of isolating these SSC from BM is dependent upon the previously noted adherence to tissue culture plastic, according to which the MNC are left to incubate for 10-14 days and in the interim CFU-F will attach and form colonies at a recognised frequency of 1:80000. At 10-14 days these CFU-F are harvested by trypsin digest and replated in serum-rich media at a density of 3-8000 CFU-F per $cm^2$. These CFU-F are then propagated in vitro until sufficient cell numbers are obtained to permit biochemical and cytological assessment. This approach is widely used but is regarded as inadequate for defining or purifying SSC for clinical use, as only 1:80,000 BMMNC plated are SSC and the methods will not comply with good manufacturing protocols needed for clinical approval of related products.

Hence, in the prior art, stem cell populations have been identified based on an initial ability to adhere to a plastic surface. From this initial screen, cell populations are obtained as clonal populations from individual colony forming units on the surface. These have also been labelled in the literature "mesenchymal stem cells" though the term may be incorrect as non-mesenchymal stem cells may be included within the isolated cells. In a known isolation approach, these known cell populations are derived from stem cells that are positive for alkaline phosphatase (ALP) and CD271. Nevertheless, in clinical terms the cell is essentially unidentified.

Cell populations are prepared from these known isolated cells, such as by clonal expansion from a single, isolated cell, and used for transplantation. The results are variable, however, in that the transplanted cell populations sometime behave rather differently from batch to batch, and with an element of unpredictability.

Prior art cell populations tend to form bone and fat and cartilage, but with limited control, frequently making fat when bone or cartilage is required. Conversely, for instance where it is preferred to obtain cells that make fat, these fat-producing cells are only obtained unreliably.

A significant problem is that the starting cell population is essentially undefined, as isolation on the basis of adherence to plastic is not a sufficiently technical definition of a cell type. Even when selected e.g. for the markers mentioned (ALP and CD271), expression of those markers in the cells or in progeny rapidly disappears upon culture, leaving an effectively undefined population. Useful properties of the cells also reduce or disappear over time—another problem with an undefined cell population.

OBJECTS OF THE INVENTION

It is an overall object of the invention to provide methods of isolation of stromal stem cells and cell populations and tissues derived therefrom that are at least an alternative to the art, and an object of particular embodiments of the invention is to provide methods that are improved, for example through increased definition of the cells obtained, or cells and tissues that are improved, for example by increased reliability of their properties, rendering them more suitable for clinical applications.

SUMMARY OF THE INVENTION

The present invention is based upon prospective isolation of stromal stem cells, especially human stromal stem cells, based on expression of markers or antigens that are expressed in a plurality of mammalian species. In methods and cell populations of the invention, cells are sorted on the basis of expression of a particular cross-species marker, this being referred to as prospective isolation, and then culture of the cells obtained, leaving to identification of cells, namely colony forming units of fibroblasts (CFU-Fs), which can be clonally expanded. The cell population obtained after the clonal expansion is then proposed for therapeutic, transplant and other uses.

Accordingly, the invention provides a method of isolation of a stromal stem cell, comprising isolation of a cell from a mixed population of mammalian cells based on expression of a marker, wherein
  the marker binds an antibody, and wherein
  said antibody cross reacts with a marker found on a cell of at least one other mammalian species selected from human, mouse, rat, horse, rabbit and pig cells.

The invention provides a method of isolation of a stromal stem cell, comprising isolation of a cell from a mixed population of mammalian cells based on expression of the marker, wherein the marker is expressed by the mammalian cell and wherein a corresponding marker is also expressed on a cell of at least one other mammalian species selected from human, mouse, rat, horse, rabbit and pig cells.

Preferably the marker is found on human stromal stem cells and mouse stromal stem cells, or on human stromal stem cells and rat stromal stem cells, or on all three. In embodiments, the marker is SDC2.

More specifically, the invention provides a method of isolation of a human stromal stem cell, comprising isolation of a cell from human bone marrow that is negative for CD45 and positive for a further cell surface marker, wherein the further cell surface marker binds an antibody and wherein said antibody cross reacts with a cell surface marker found on a cell of at least one other mammalian species selected from mouse, rat, horse, rabbit and pig cells. More specifically, the invention provides a method of isolation of a human stromal stem cell, comprising isolation of a cell from human bone marrow that is positive for FAP alpha and positive for a further cell surface marker, wherein the further cell surface marker binds an antibody and wherein said antibody cross reacts with a cell surface marker found on a cell of at least one other mammalian species selected from mouse, rat, horse, rabbit and pig cells.

Preferably the further marker is found on human stromal stem cells and mouse stromal stem cells, or on human stromal stem cells and rat stromal stem cells, or on all three. In embodiments the further marker is NG2 or, in particular, SDC2.

Methods of obtaining a population of cells are also provided, comprising isolating cells according to the invention, and deriving the population from those isolated cells; and methods of obtaining a clonal population of cells are provided, comprising isolating a single cell according to the invention and deriving a clonal population of cells from the single cell.

The cells thereby obtained are also provided by the invention—hence, populations of stromal cells, preferably stromal stem cells, enriched with respect to the marker. Enrichment may be to 30% or more, 35% or more, or 40% or more cells being positive for the marker. In embodiments, the marker is NG2 or, in particular SDC2.

A specific population of cells of the invention is obtained by:—
providing a human stromal stem cell,
deriving a clonal population of cells from the human stromal stem cell, and
optionally, further growing and/or expanding and/or passaging the cells in culture, wherein the human stromal stem cell is isolated from bone marrow, is negative for expression of CD45 and is positive for expression of a further cell surface marker, wherein the further cell surface marker binds an antibody and wherein said antibody cross reacts with a cell surface marker found on a cell of at least one other mammalian species selected from mouse, rat, horse, rabbit and pig cells.

A further specific population of cells of the invention is obtained by:—
providing a human stromal stem cell,
deriving a clonal population of cells from the human stromal stem cell, and
optionally, further growing and/or expanding and/or passaging the cells in culture, wherein the human stromal stem cell is isolated from bone marrow, is positive for expression of FAP alpha and is positive for expression of a further cell surface marker, wherein the further cell surface marker binds an antibody and wherein said antibody cross reacts with a cell surface marker found on a cell of at least one other mammalian species selected from mouse, rat, horse, rabbit and pig cells.

Products from the cells, such as bone, cartilage tendon and other stromal stem cell products are provided by the invention, as are use of the cells e.g. in assays.

The invention enables identification of desired stromal stem cells on the basis of specific marker expression, providing prospectively purified and defined cells and populations derived therefrom.

DETAILS OF THE INVENTION

Hence, the invention provides a method of isolation of a stromal stem cell, comprising isolation of a cell from a mixed population of mammalian cells based on expression of a cell surface marker, wherein
the cell surface marker binds to an antibody, and wherein said antibody cross reacts with a cell surface marker found on a cell of at least one other mammalian species selected from human, mouse, rat, horse, rabbit and pig cells.

The antibody may recognize a cell surface marker on a human cell and cross react with a cell surface marker on at least one other mammalian cell selected from mouse, rat, horse, rabbit and pig cells. In use, such methods are suitable for isolation of human, mouse, rat, horse, rabbit and pig cells, in particular human cells.

The antibody may recognize a cell surface marker on an equine cell and cross react with a cell surface marker on at least one other mammalian cell selected from human, mouse, rat, rabbit and pig cells. In use, such methods are suitable for isolation of human, mouse, rat, horse, rabbit and pig cells, in particular equine cells.

Similarly, the invention provides a method of isolation of a stromal stem cell, comprising isolation of a cell from a mixed population of mammalian cells based on expression of a cell surface marker, wherein the cell surface marker is expressed by the mammalian cell and wherein a corresponding cell surface marker is also expressed on a cell of at least one other mammalian species selected from human, mouse, rat, horse, rabbit and pig cells.

The marker may be expressed on a human cell and the corresponding marker may be expressed on at least one other mammalian cell selected from mouse, rat, horse, rabbit, and pig cells, for isolation e.g. of human cells. The antibody may be expressed on an equine cell and the corresponding marker expressed on at least one other mammalian cell selected from human, mouse, rat, rabbit and pig cells, for isolation e.g. of equine cells. A marker is a corresponding marker if an antibody can be used to sort human cells based on binding to a marker on human cells and that same antibody can be used to sort cells of another mammalian species.

Prospective stromal stem cell isolation of the invention thus uses markers found across species, referring to binding of markers in different mammalian species to a common antibody. In a specific embodiment described below, antibody to human SDC2 binds to and can be used to isolate human stromal stem cells and binds also to and can be used to isolate stromal stem cells in mouse, rat, horse and rabbit.

The antibody may bind to or cross react with markers on cells of at least three mammalian species, at least four or at least five species.

Separately, the invention provides a method of obtaining or deriving a stromal stem cell population comprising prospective isolation of cells based on expression of a marker that is similarly expressed in human and at least one other of mouse, rat, rabbit, horse and pig cells, for isolation e.g. of human stromal stem cells.

In embodiments of-the invention, stromal stem cells are isolated according to expression of a marker expressed in at least human and mouse stromal stem cells, in at least human and rat stromal stem cells or in at least human, mouse and rat stromal stem cells. Hence, for example, an antibody to SDC2 can be used to isolate corresponding populations of stromal stem cells in human, mouse, rabbit, horse and rat. Other known antibodies, to NG2 and FAP alpha, details of which are below, can be used to isolate corresponding populations of stromal stem cells in human, mouse and rat. Corresponding stromal stem cell populations, and derivatives thereof, from both or all three species can therefore be obtained in parallel or for comparison or to perform analysis of stromal cells of one species prior to work on stromal stem cells of another.

Various sources of the starting cells from which to isolate the stem cells are suitable. A source, a mixed population of mammalian cells, can be bone marrow, adipose tissue, skeletal muscle, endometrium, placenta, umbilical cord, umbilical cord blood and Wharton's jelly. Sources of human, mouse, rat, rabbit, equine and pig cells can be used, and in specific examples human cells have been used. One source used in examples is bone marrow, and a specific preferred source is human bone marrow. Another source is cells, e.g. SSCs, derived from human pluripotent cells. In an example, human SSCs from hES cells were used.

In use of the invention, an initial sort may be performed on the basis only of the first marker, e.g. SDC2 expression. This method generally also isolates unwanted cells, meaning cells that are not stromal stem cells and may be e.g. B-cells or T-cells. By the further step of isolating CFUs, however, these unwanted cells may be lost as they do not form colonies, so this level of sorting may be acceptable as only the desired, stromal cells capable of forming CFUs will then produce clonal populations.

In certain embodiments of the invention, cells are isolated based on expression of two separate markers. The combination selection of cells may be selection for positive/positive cells, meaning cells are selected if they are positive for expression of the first marker and positive for the expression of the second marker. The selection may also be for positive/negative, for negative/positive or for negative/negative.

A combination method of the invention, typically combining one or more or all features of any method described elsewhere heroin, therefore comprises isolating cells on the basis of expression of a further cell surface marker different from the first. This may be referred to as the second marker, though the nomenclature is to indicate merely that the markers are different from one another and does not indicate a temporal difference in the timing of selection or isolation according to that marker. The selection based on markers may be sequential, in either order, though commonly is carried out in a single sorting or isolation, which can be simultaneous, as technology available enables this.

One suitable second marker is CD45. Suitably, cells that are CD45 negative are selected. A further suitable marker is FAP alpha; suitably the FAP alpha positive cells are selected. Suitable first cell surface markers include SDC2 and NG2.

In another use of the invention, an initial sort is carried out on the basis of CD45 expression, the negative fraction being selected. A separate sort is carried out on the basis of the first marker, e.g. SDC2, expression. The positive fraction can be taken or the negative fraction can be taken. In practice, the sorting is generally carried out simultaneously. Cell viability can be dramatically reduced in sequential sorting.

In a particular method of the invention, cells positive for the first marker are selected; these methods are suitable for isolation of osteogenic cells and angiopoietic cells.

In another particular method of the invention, cells that are negative for the first marker are selected; these methods are suitable for isolation of adipogenic cells.

A specific method of isolation of a human stromal stem cell comprises isolation of a cell from human bone marrow that is positive for a first marker and negative for CD45, wherein the first marker binds an antibody and wherein said antibody cross reacts with a marker found on a cell of at least one other mammalian species selected from mouse, rat, horse, rabbit and pig cells. The first marker is preferably SDC2 and isolation uses an antibody that binds SDC2 and cross reacts with a corresponding marker on all of human, mouse, rat, horse, rabbit. The first marker may be NG2 and isolation uses an antibody that binds human NG2 and cross reacts with a marker corresponding to NG2 on one or more of mouse, rat, horse, rabbit and pig cells.

Combination marker sorting can also comprise sorting according to three different markers, for example on the basis of the second marker and then two or more first markers. Sorting by NG2 can be used to subdivide the SDC2+ve population.

Specific isolated stromal stem cells of the invention are:—
(i) CD45 −ve, SDC2+ve
(ii) CD45 −ve, SDC2 −ve
(iii) CD45 −ve, SDC2+ve, NG2+ve
(iv) CD45 −ve, SDC2+ve, NG2 −ve
(v) FAP alpha +ve, SDC2+ve
(vi) FAP alpha +ve, SDC2 −ve
(vii) FAP alpha +ve, SDC2+ve, NG2+ve
(viii) FAP alpha +ve, SDC2+ve, NG2 −ve From cells that have been isolated, cell cultures and populations can be obtained. This can be achieved by clonal expansion of an isolated cell (e.g. a cell that is at least initially CD45 negative and SDC2 positive or CD45 negative and SDC2 negative) and then continued growth or culture of the cells obtained. Note that the cells obtained by this continued growth and culture and passaging tend initially to demonstrate the same marker spectrum as the originally isolated cell or cells. Over time the expression pattern may change. But the properties of the resultant population are linked to the criteria of the initial isolation (e.g. a cell that is at least initially CD45 negative and SDC2 positive or CD45 negative and SDC2 negative).

From cells that have been isolated, cell cultures and populations can generally be obtained having a high homogeneity, measured by expression of the marker or antigen used for the isolation. Hence, mammalian stromal cell populations are also provided by the invention expressing high levels of the first cell surface marker. The % of cells expressing the first marker may be 50% or more, 60% or more, 70% or more, 75% or more, 80% or more, or 90% or more. In a specific embodiment of the invention described below in more detail, initial cell populations express the first marker at a level of 95% or more. In referring to cells that are positive, reference is to positive as measured at or on the cell surface, e.g. as detectable using a labelled antibody to the marker.

Cells populations may also be derived from the above, for example by culture and/or passaging, and in doing so the proportion of cells that retain expression of the first marker may reduce, but nevertheless remain higher that in populations not selected on the basis of the marker. Hence, further mammalian cell populations are also provided by the invention expressing high levels of the first marker. The % of cells expressing the first marker may be 30% or more, 40% or more, 50% or more, or be at the levels recited immediately above. The cell populations of the invention have specified purity and are defined. The cells can be identified/selected on the basis of marker expression and used immediately, with no need for culture to determine if a sufficiently pure population of cells has been obtained.

In particular embodiments of the invention the marker is NG2 or, especially, SDC2.

A population of mammalian stromal stem cells is thus provided, wherein 75% or more of the cells are positive for a cell surface marker, and wherein a corresponding cell surface marker is also expressed on a cell of at least one other mammalian species selected from human, mouse, rat, horse, rabbit and pig cells. The marker is suitably expressed on a human cell and the corresponding marker is expressed on a mouse cell and optionally also on at least one other mammalian cell selected from rat, horse, rabbit and pig cells. The marker is suitably expressed on a human cell and the corresponding marker is expressed on a rat cell and optionally also on at least one other mammalian cell selected from mouse, horse, rabbit and pig cells. In another exemplary population of stromal stem cells, 75% or more of the cells are SDC2 positive, and these cells were osteogenic. Further, the cells may additionally be characterised by expression levels of the second marker. The % of cells expressing the second marker may be 50% or more, 60% or more, 70% or more, 75% or more, 80% or more, or 90% or more. In a specific embodiment of the invention described below in more detail, 95% or more of cells in the initial cell populations are positive for the second marker. The cells may separately be negative for the second marker. The % of cells not expressing the second marker may be 50% or more, 60% or more, 70% or more, 75% or more, 80% or more, or 90% or more. In a specific embodiment of the invention described below in more detail, 95% or more of cells in the initial cell populations are negative for the second marker. In one exemplary population of osteogenic and angiopoietic stromal stem cells, 75% or more of the cells are SDC2 positive and 75% or more of the cells are CD45 negative.

Cell populations are also provided by the invention expressing low levels of the first marker. The % of cells not expressing the first marker may be 50% or more, 60% or more, 70% or more, 75% or more, 80% or more, or 90% or more. In a specific embodiment of the invention described below in more detail, initial cell populations express the first marker at a level of 5% or less or are regarded as negative for that first marker. In one exemplary population of stromal stem cells, 75% or more of the cells are SDC2 negative, and are adipogenic cells. Further, the cells may additionally be characterised by expression levels of the second marker. The % of cells expressing the second marker may be 50% or more, 60% or more, 70% or more, 75% or more, 80% or more, or 90% or more. The cells may separately be negative for the second marker. The % of cells not expressing the second marker may be 50% or more, 60% or more, 70% or more, 75% or more, 80% or more, or 90% or more. In a specific embodiment of the invention described below in more detail, 95% or more of cells in the initial cell populations are negative for the second marker. In one exemplary population of adipogenic stromal stem cells, 75% or more of the cells are SDC2 negative and 75% or more of the cells are CD45 negative.

Accordingly, the invention also provides a method of obtaining a population of cells, comprising isolating cells according to the methods described and deriving the population from those isolated cells; and the invention further provides a method of obtaining a clonal population of cells, comprising isolating a single cell according to the methods described and deriving a clonal population of cells from the single cell. Generally, culture comprises obtaining an initial population of cells and then further growing and/or expanding and/or passaging the cells in culture. SDC2 is the characterising marker in specific examples described below.

Cell populations described in specific examples below have been obtained and found to exhibit useful properties. Hence, still further provided by the invention are a population of cells obtainable according to the described and claimed methods. The cell populations are preferably human, equine, rabbit, mouse and/or rat cells.

A population of cells of a specific embodiment is obtained by:—
  providing a human stromal stem cell,
  deriving a clonal population of cells from the human stromal stem cell, and
  optionally, further growing and/or expanding and/or passaging the cells in culture, wherein the human stromal stem cell is isolated from bone marrow, is negative for expression of CD45 and is positive for expression of a further cell surface marker, wherein the further cell surface marker binds an antibody and wherein said antibody cross reacts with a cell surface marker found on a cell of at least one other mammalian species selected from mouse, rat, horse, rabbit and pig cells.

Tissues are provided by the invention, by obtaining cells according to described methods, and obtaining tissue therefrom. Tissue selected from bone, cartilage and tendon can be obtained in this way. Adipose tissue or tissue for reconstructive surgery can also be obtained.

A further use of the invention lies in providing cells for and assays using the isolated cells and progeny thereof. Hence, a method of conducting an assay comprises obtaining cell according to the described methods, and using those cells in the assay.

Prior art cell populations, as mentioned, tended to form bone and fat and cartilage, with limited control and thus sometimes making fat when bone or cartilage is required. Cell populations of the invention can be prepared that tend not to form fat. This is an advantage. Separate cell populations of the invention can be prepared that do indeed tend to form fat. The user may thus be provided with enhanced control and predictability of the properties of the cells, based on a specific cell marker selection criterion.

An advantage of specific cell populations of the invention can be put another way, namely for the CD45 negative, SDC2 positive cells that they tend to be osteogenic, generating bone—and cartilage-producing cell populations with higher frequency. The prior art difficulty of mixed results and low reproducibility of obtaining bone and cartilage may thereby be solved. Specific cell populations now obtainable may have further advantages; e.g. SDC2 positive populations appear to be more angiopoeitic, inducing neighbouring cells to form vasculature. This is advantageous in treating diseases that would benefit from improved vasculature, for example ischemic diseases.

In addition, SDC2 positive populations are derived in specific methods of the invention from starting cells that are more highly defined than in the prior art, by reference to a marker that persists in cells and progeny. In itself, this is an advantage. The cell population is an acceptably defined population.

A further potential advantage of the invention is that the marker used for prospective isolation of the initial cell population is also useful for prospective isolation of cell populations in other species. Thus, in a specific embodiment, SDC2 is common across all of human, mouse, rat, horse, rabbit. As a result, it is possible to isolate a corresponding population in, say, mouse cells and then extrapolate from work on mouse cells to work on human cells. A defined population in the mouse can be used to obtain data which can then be taken further, in a corresponding defined population in another species, especially human cells. A problem believed to be true for prior art mesenchymal stem cell populations, i.e. those obtained using a known prospective isolation, is that the marker used for isolation, say, of the mouse cells does not have a corresponding pattern of expression in the human cells. The invention may thus provide defined cell populations with cross species parallel populations, such as mouse and human or mouse and equine, etc. This facilitate pre-clinical and clinical work because knowledge obtained from experiments carried on initially on cells of one species can be transferred to late work on the corresponding defined cell population in another species.

Cells and tissue of the invention, and compositions comprising the cells and tissues, can be used to treat various mammalian conditions and diseases, including in particular those treatable using cells and products derived from existing SSC products. The cells and tissue may interact with dendritic cells and drive IFN-β secretion, and hence may be used as a tumor suppressor. Cancers in general may be treated using the invention, specifically including hepatocellular carcinoma, cervical cancer, pancreatic cancer, prostate cancer, fibrosarcoma, medullablastoma, and astrocytoma. Lung diseases may be treated including Acute lung injury (ALI); Acute respiratory distress syndrome (ARDS); Chronic Obstructive Pulmonary Disorder (COPD); Idiopathic pulmonary fibrosis (IPF). The cells and tissues may be used to treat sepsis and sepsis-induced multiorgan failure, bone marrow transplant (BMT) or haematopoietic stem cell (HSC) rejection; solid organ transplant (SOT) rejection (including liver, kidney, skin, cornea, heart, lung); acute toxin-induced liver failure; autoimmune hepatitis; primary biliary cirrhosis (PBC) and primary sclerosing cholangitis (PSC); osteonecrosis; degenerative disc disease; rheumatoid arthritis; osteoarthritis and delayed bone healing in diabetic patients; autoimmune nephritis including Wegener's granulomatosis (WG); burns, severe burns; muscle wasting conditions and atrophic syndromes including sarcopenia; cachexia and other muscle wasting conditions including the muscular dystrophies (Duchenne and Becker); congestive heart failure, acute myocardial infarction and stroke; type 1 diabetes; type 2 diabetes; diabetic retinopathy and other retinopathies; diabetic nephropathy and other nephropathies; diabetic neuropathy and other neuropathies; non-healing diabetic ulcers; diabetic cardiomyopathy and other myopathies; athersclerosis; peripheral artery disease and critical limb ischemia; uveitis; (wet or dry) acute macular degeneration (AMD); retinal and corneal damage; autoimmune conditions such as autoimmune gastritis (AIG); graft-versus-host disease (GvHD); multiple sclerosis and demyelinating diseases; thyroid disease; inflammatory bowel diseases including Crohn's Disease, Ulcerative colitiis and fistulising Crohn's disease; scleroderma; lupus (SLE); Graves' Disease; and autoimmune lymphoproliferative disease (ALPS).

The cells and tissue may also be used to treat particular various equine conditions, including laminitis, tendon injuries and exercise induced pulmonary haemorrhage (EIPH)—also known as "bleeding" or a "bleeding attack".

Also provided by the present invention is a pharmaceutical composition for treating a disease or disorder in an animal, in particular a mammal and for example a human or horse. The pharmaceutical composition suitably comprises cells or tissue of the invention in an amount effective to treat the disease or disorder in the animal. The cells may thus be administered with an acceptable pharmaceutical carrier. For example, the cells may be administered as a cell suspension in a pharmaceutically acceptable liquid medium for injection. Examples of liquid medium are saline, phosphate buffered saline, optionally also containing additional materials such as dimethylsufoxide (DMSO) and human serum albumin. The cells and tissue may generally be administered in a variety of formats as known for existing mesenchymal stem cell and like products and tissue derived therefrom. They can be administered systemically, e.g. by intravenous infusion, or direct injection. The compositions may comprise a matrix or scaffold, or cells or tissue may be administered by injection into a site already comprising matrix or scaffold in situ. The cells or tissue may thus be administered in combination with hyaluronic acid, collagen or other extracellular matrix. Further formulation and administration examples that can be applied mutatis mutandis to the cells and tissue of the invention may be found in the art, e.g. in WO2001080865, EP2545928 and WO1999061587. A method of treatment of an animal is provided, comprising administering to the animal a composition of the invention. Cells or tissue according to the invention are provided for use in treatment of a disease or disorder of an animal. Embodiments of the methods and uses comprise embodiments generally of the invention as described herein.

Suitable antibodies are available to the skilled person for performing sorting and isolation based on the identified markers. A human NG2/MCSP Antibody is available from R&D Systems, Inc. (614 McKinley Place NE, Minneapolis, MN 55413, USA), as a monoclonal Mouse lgG1 Clone #7.1, Catalog Number: MAB25851. A NG2 (G-20) antibody is available from: Santa Cruz Biotechnology, Inc. (2145 Delaware Avenue, Santa Cruz, California, 5060, USA), ref: sc-30923, reactive with mouse, rat, human, equine, canine, bovine and porcine; the blocking peptide, sc-30923 P, is also available. A Human Fibroblast Activation Protein a/FAP Antibody, catalog Number: AF3715, is available from R&D Systems, Inc. A FAPalpha (Y-16) antibody is available from Santa Cruz Biotechnology, Inc. reactive with at least human, rat and mouse and also equine, canine, bovine, porcine and avian. An Anti-Fibroblast activation protein, alpha antibody, ab28243, is available from Abcam (330 Cambridge Science Park, Cambridge, CB4 0FL, UK) reactive with at least mouse, rat and human. A Syndecan 2 antibody, orb13481, reactive with at least human, mouse and rat is available from Biorbyt Ltd. (12 Pembroke Avenue, Denny Industrial Centre, Waterbeach, Cambridge, CB25 9QR, UK). The SDC2 antibody used in specific examples, catalog number: MAB29651 (Clone 305507) is available from R&D Systems, Inc, reactive with human, mouse, rat, equine, rabbit and pig.

SDC2, also called Fibroglycan and now, CD362, was originally biochemically characterized as one of the major heparan sulfate (HS) glycosaminoglycan (GAG)-containing cell surface proteins expressed in the lung. SDC2 is one of four members of this single-pass transmembrane family in vertebrates. Herein, reference to "S2" and "SDC2" refer to SDC2.

The invention is now described in specific embodiments with reference to the accompanying drawings in which:

FIG. 1 shows labelling by anti-SDC2 antibody of human stromal stem cells but not human lung fibroblasts. Green lines indicate anti-SDC2– APC staining of cells. Red lines indicate labelling with appropriate control antibody (Rat lgG2B Isotype Control-APC; R&D #IC013A; Clone—141945). Blue lines indicate positive control labelling of MRCS with anti-PDGFRa-APC antibody (R&D Systems #FAB1264A; Clone—PRa292);

FIG. 2 shows labelling by SDC2-APC antibody of $CD271^{bright/DC45low}$ human bone marrow mononuclear cells. Data show fluorescence-activated Cell Sorting (FACS) profile of $3.5 \times 10^7$ BMMNCs stained with aforementioned SDC2-APC, CD271-PE and CD45-FITC (both from BD). CD45-FITC staining permitted gating of BMMNCs into 3 populations, (A) CD45-ve—BLUE, (B) CD45low—ORANGE, and (C) CD45high—GREEN. In (B) rare TP SDC+ve/CD271 bright/CD45low cells are BLUE;

Figure 1:
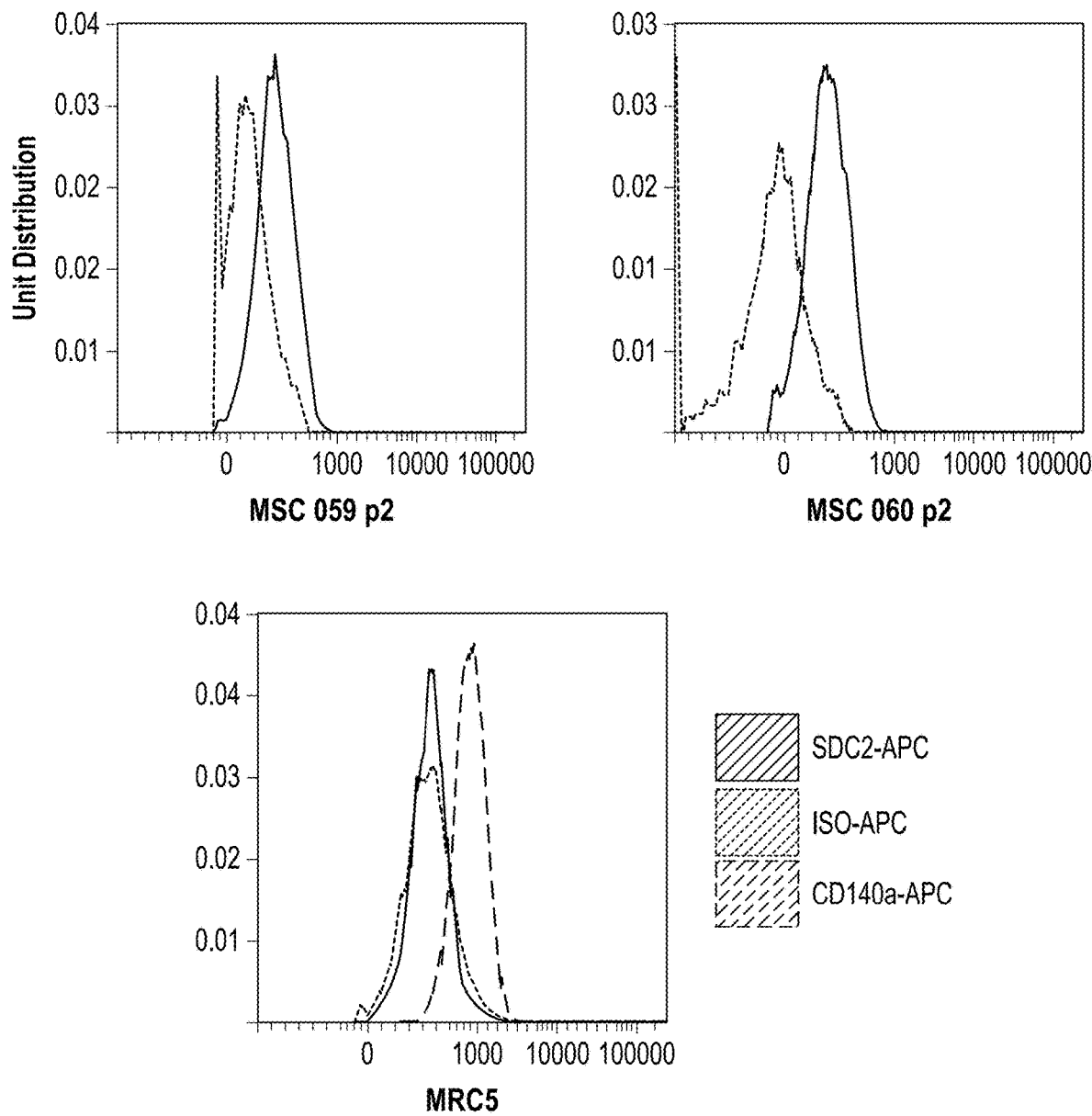

We used a rat lgG2B monoclonal antibody to human SDC2 conjugated to the Allophycocyanin (APC) fluorochrome (R&D Systems number FAB2965A; clone 305515) to indicate if expression of SDC2 protein is enriched on the cell surface of human SSC in comparison to a control human foetal lung fibroblast cell line, MRCS. MRCS lung fibroblasts cultured in SSC growth media (aMEM/10% PAA FSC; NUNC T175 flasks) did not express SDC2 (FIG. 1). As a control, we show that MRCS fibroblasts do express the PDGFRa marker (CD140a-APC). These data suggests that expression of SDC2 protein is enriched on the surface of human SSC in comparison to control lung fibroblasts (FIG. 1).

At this time, the state of the art for antibody-based purification of SSC from BM consists of using a combination of anti-CD271 (LNGFR) and anti-CD45 antibodies, reported by University of Leeds (Drs. McGonagle and Jones). This isolation of CD45low/CD271 bright cells has been shown to capture all CFU-F (SSC).

However, the definition of CD271 'bright' cells can be difficult to standardise from lab to lab. To investigate if this anti-SDC2 antibody co-stains CD45low/CD271 bright BMMNCs, 30 ml of human BM was aspirated from donor CRFG #0007 at the Clinical Research Facility (CRF) at Galway University Hospital (GUH) by Dr Ruth Morrell.

BMMNCs ($5 \times 10^8$) were isolated by Ficoll centrifugation, washed in PBS, resuspended in MACS buffer and blocked with Human FC-Block (Miltenyi, UK). BMMNCs ($4 \times 10^7$) were stained with anti-SDC2-APC (R&D), anti-CD271-PE (BD) anti-CD45-FITC (BD) and Sytox/DAPI viability dye. Cells were analysed by FACS on the Becton Dickinson Ariall at NUI Galway.

Figure 2:
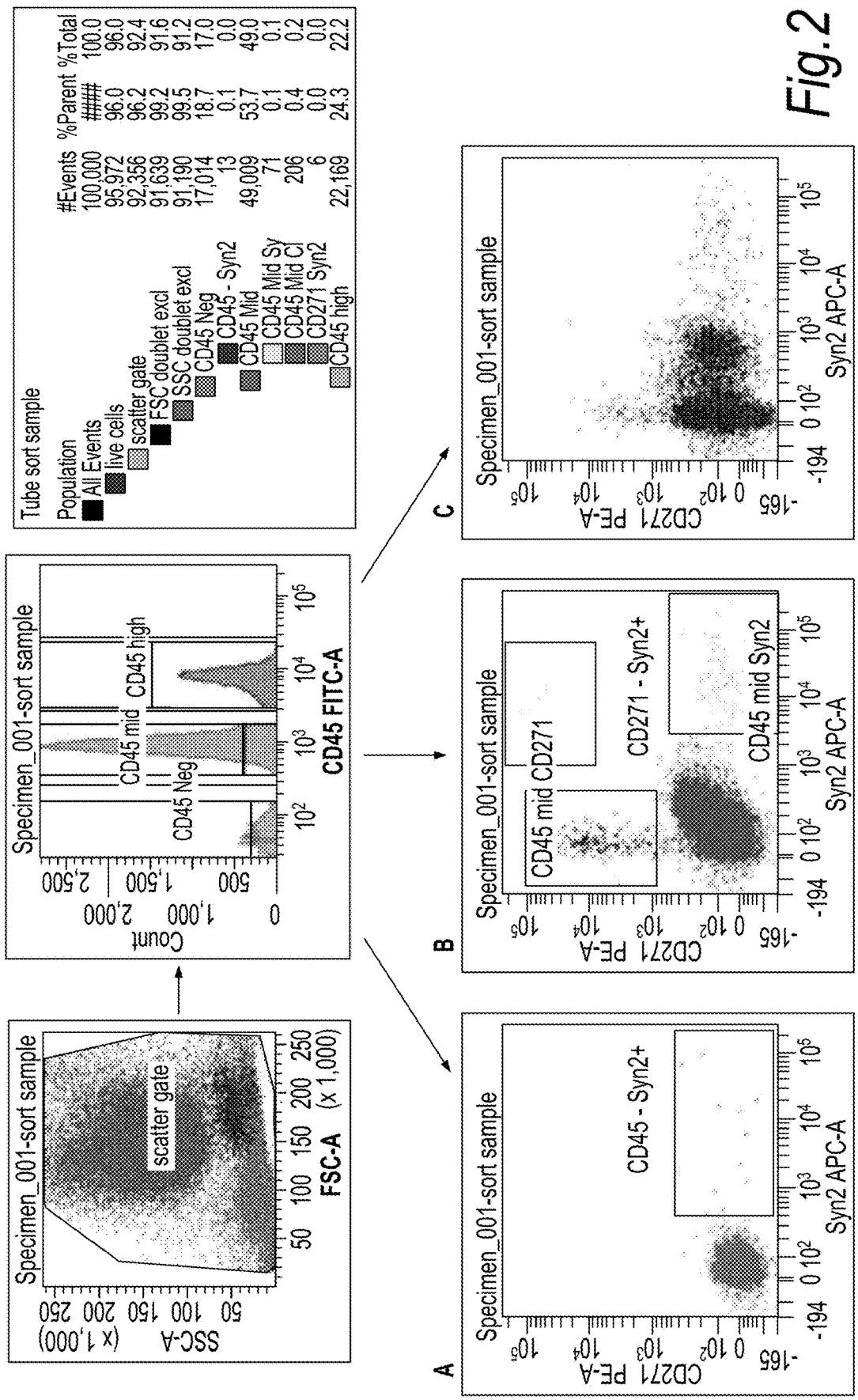

FIG. 2 indicates representative histogram/dot plots from SDC2/CD271/CD45 triple stained cytometry experiments. FIG. 2B indicates BMMNCs that express low/mid levels of the CD45 marker (orange). In agreement with other reports, we find that CD271-positive cells are found within the CD45low population (FIG. 2B) and in these experiments, we noted that the anti-SDC2-APC antibody labelled CD45low/CD271-positive cells. Specifically, the anti-SDC2-APC antibody labels CD45low/CD271 bright BMMNCs. The SDC2+/CD45low/CD271+ triple positive (TP) population are rare within BMMNCs with a frequency ranging from 1:16,000 to 1:23,000.

Figure 3:
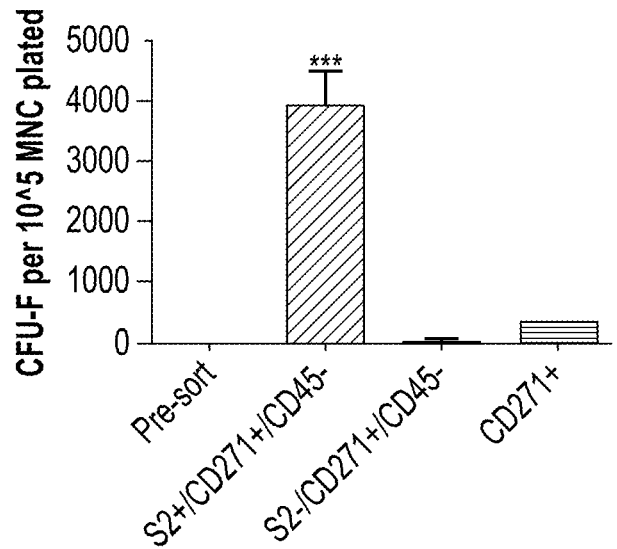
FIG. 3 shows enhanced enrichment in CFU-F in SDC+/$CD271_{bright}/DC45^{low}$ sorted bone marrow mononuclear cells. Data show fluorescence-activated Cell Sorting (FACS) profile $10^7$ BMMNCs stained with aforementioned SDC2-APC, CD271-PE and CD45-FITC (both from BD)
Figure 4:
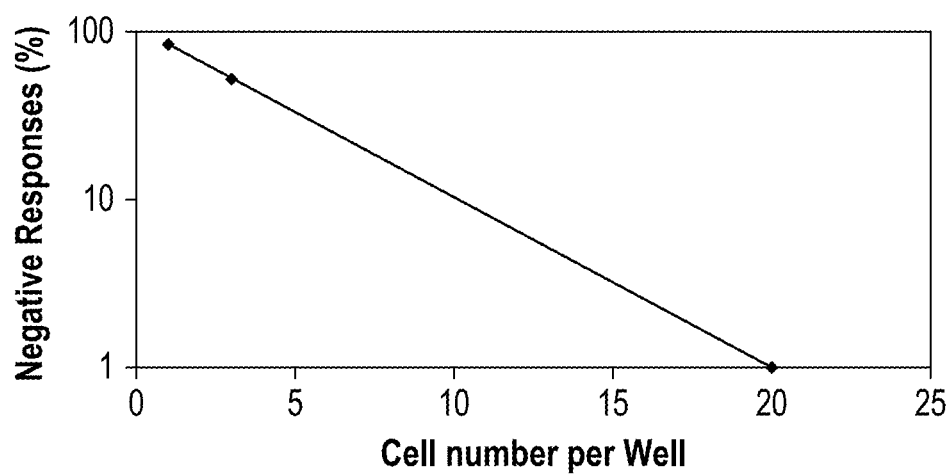
FIG. 4 shows percentage of wells of a 96 well plate in which no clone formed as function of number of SDC+/$CD271^{bright}$/CD45-mononuclear cells per cell.
Figure 5:
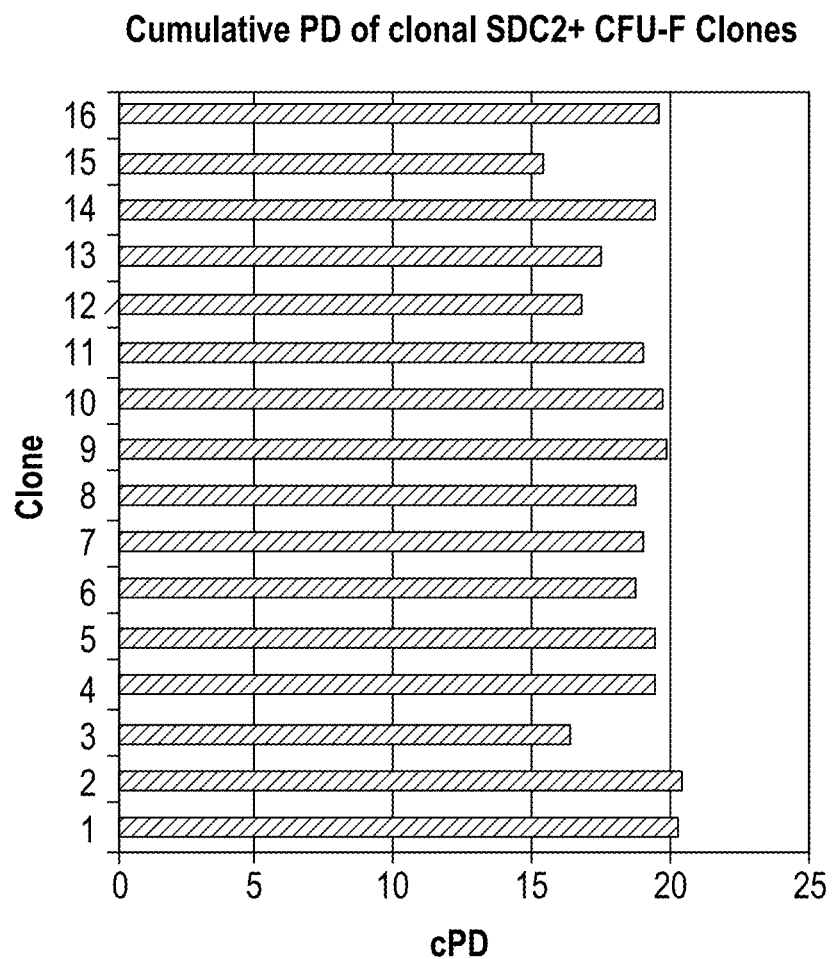
FIG. 5 shows the number of population doublings of clones.
Figure 6:
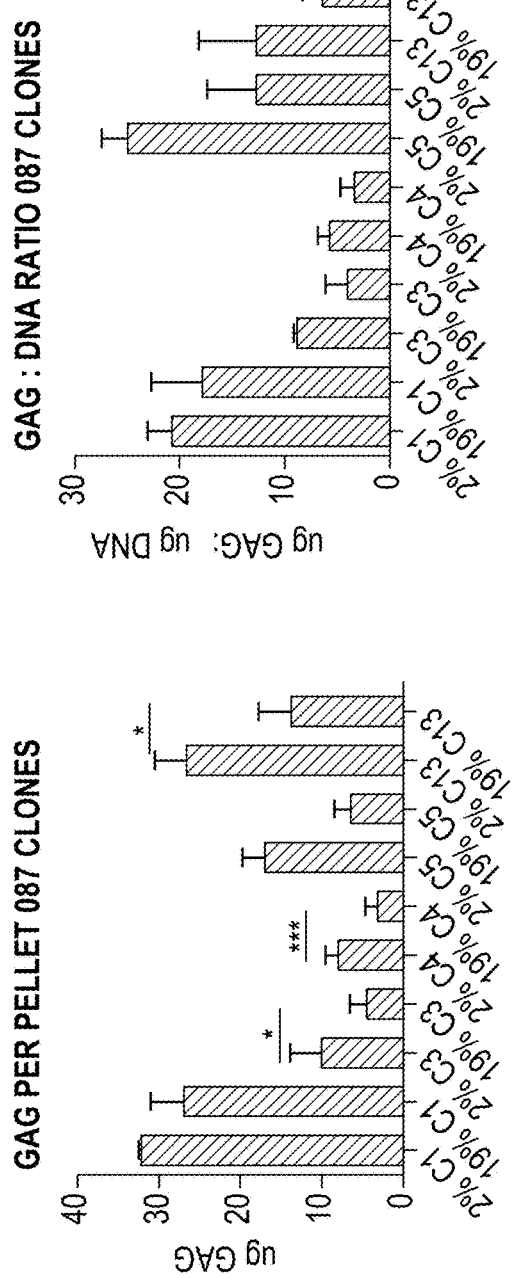
FIG. 6 shows in vitro GAG deposition of SDC2+ stromal stem cells at 2% and 19% oxygen tension. Representative Safranin-O stained histology sections from SDC2+SSC derived micromass pellets are shown.
Figure 6:
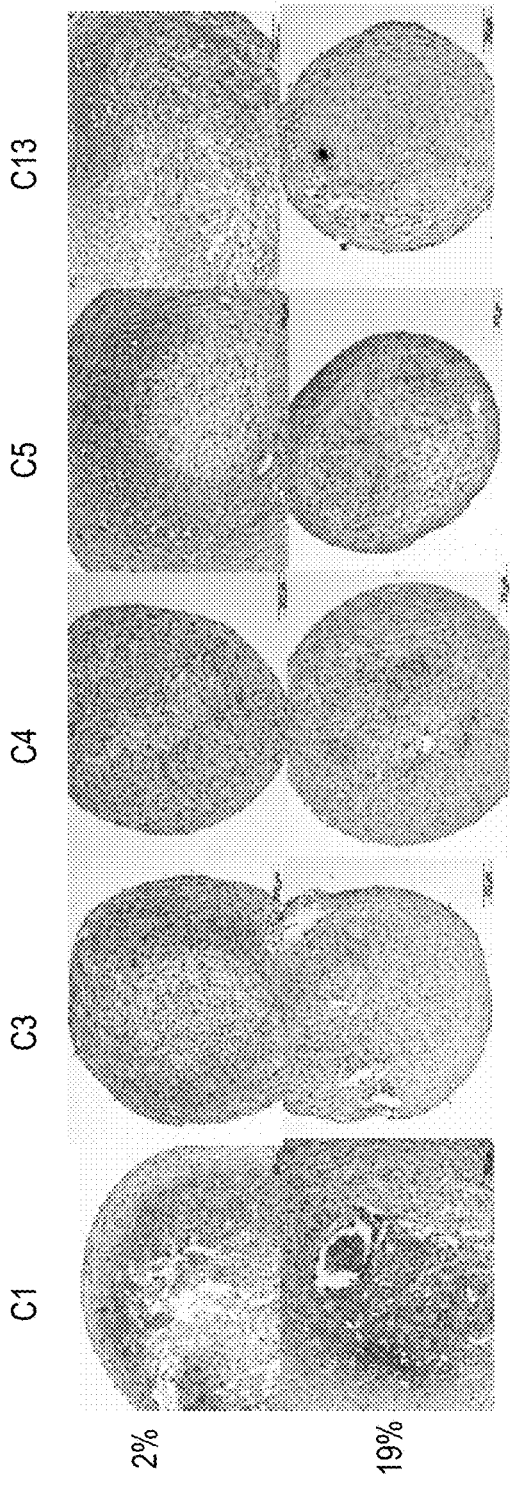

FIG. 3 shows that SDC2+/CD271+/CD45– MNC fraction contain 3000-fold more CFU-F/SSC compared to native pre-sorted BMMNCs. Conversely the SDC2-negative fraction of the CD271+ population does not retain a significant number of CFU-F/SSC Single cell FACS sorting experiments were performed to enumerate the number of clonogenic cells within the SDC2+/CD271+ population. Single SDC2+/CD271+/CD45– MNC were sorted at 1, 3 and 20 cells per well in a 96 well plate. A limiting dilution analysis reveals that, at 1 cell per well, 16-17 clones formed per 96 well plate (FIG. 4). All 16 clones were proliferative and able to undergo 15-20 population doublings (FIG. 5). Notably, selected SDC2+ clones were able to undergo significant chondrogenesis in response to in vitro micromass culture. All five clones exhibited enhanced glycosaminoglycan (GAG) deposition when cultured in low (2%) tensions of oxygen (FIG. 6).

Figure 7:
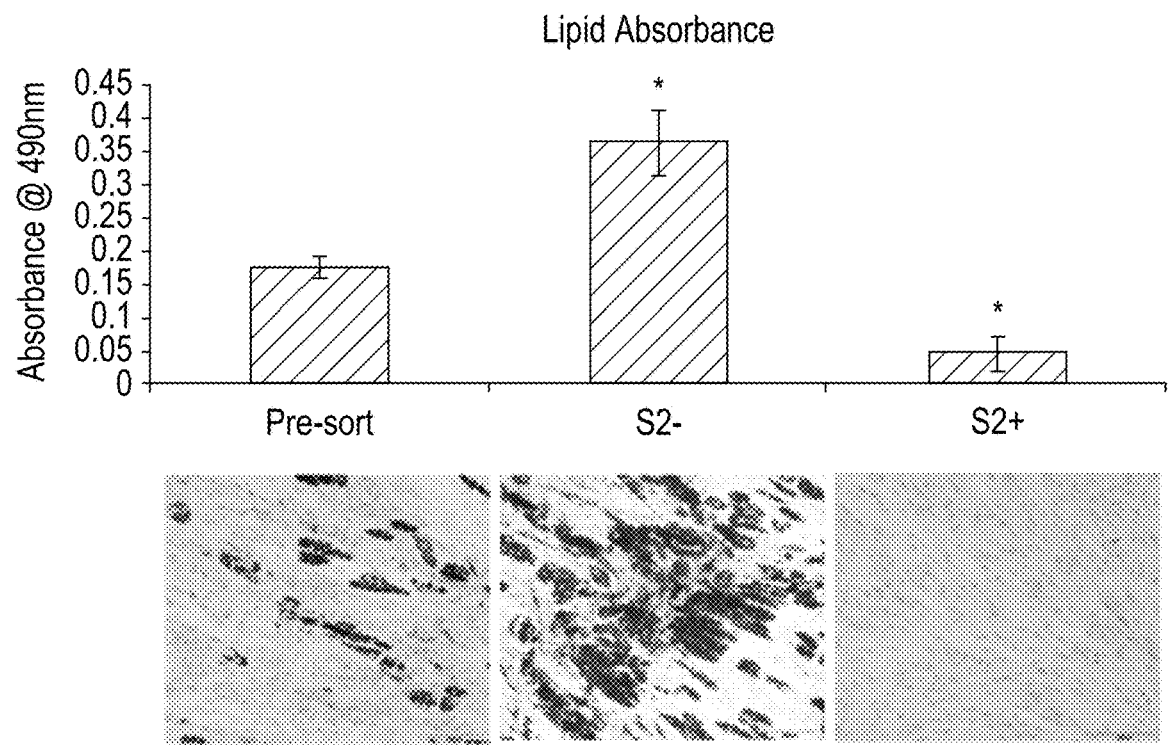
FIG. 7 shows in vitro lipid deposition of SDC2+ and SDC2– (labelled as S2+ and S2– respectively) stromal stem cells.
Figure 8:
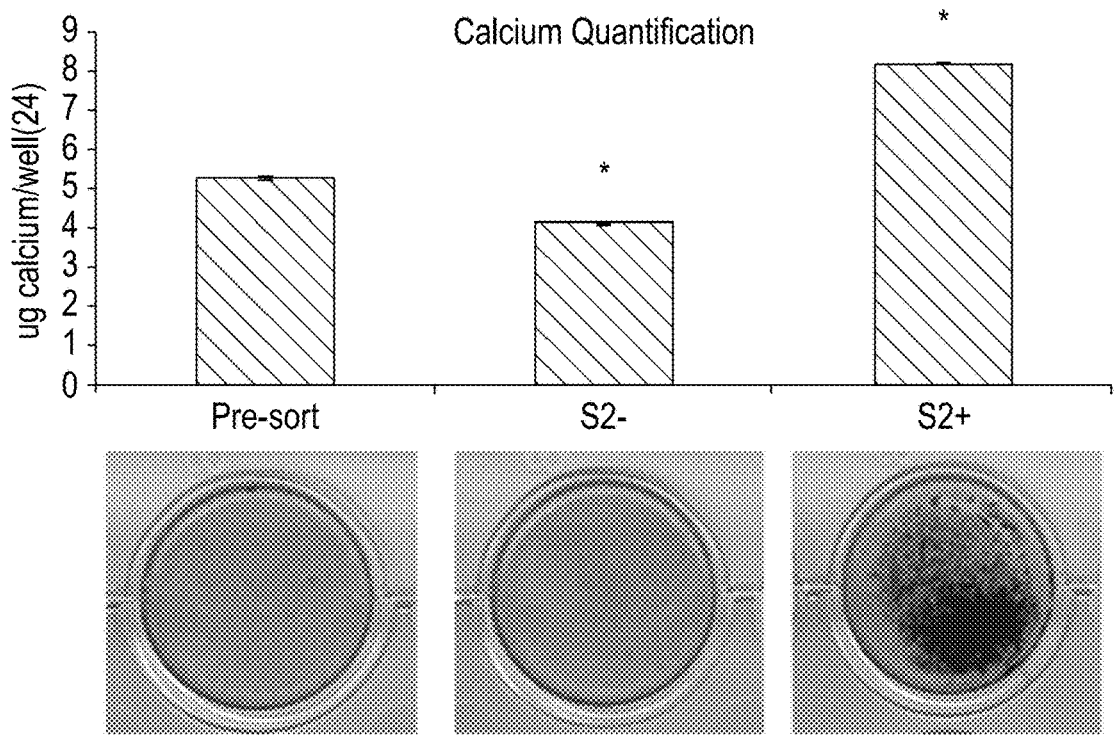
FIG. 8 shows calcium deposition of SDC2+ and SDC2– stromal stem cells in response to in vitro osteogenic stimuli.
Figure 9:
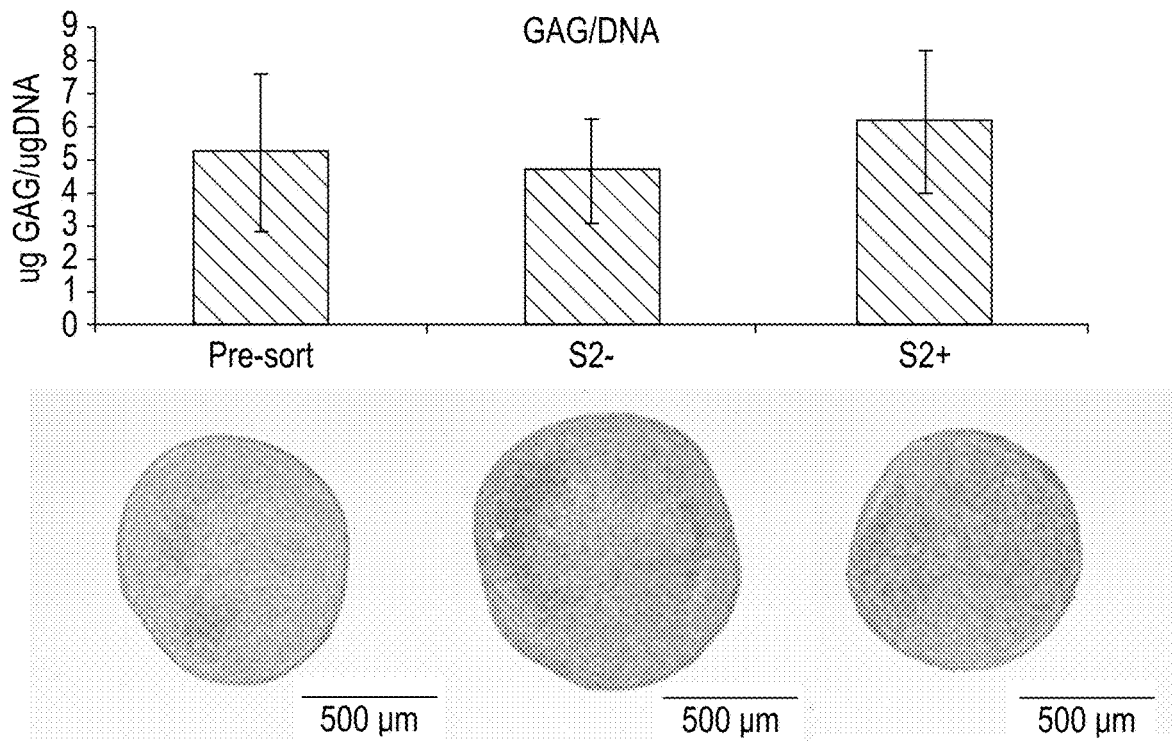
FIG. 9 shows GAG deposition of SDC2+ and SDC– stromal stem cells in response to in vitro chondrogenic stimulation.

When compared to pre-sorted (parental) SSC, FACS-sorted and culture expanded SDC2+SSG exhibit significantly attenuated deposition of lipids in response to in vitro stimulation with potent adipogenic media over a 14 day differentiation regimen (FIG. 7), as visualised with Oil Red O staining, extractions and quantification. Conversely, compared to SDC2 –SSC and pre-sort SSC, SDC2+ SSC elicit enhanced deposition of calcium and enhanced matrix mineralisation in response to a 14 day induction with an osteogenic media, as measured by calcium extraction and Alizarin Red S staining respectively (FIG. 8). Notably, no difference was observed between the three populations of SSC when subjected to chondrogenic micromass culture (FIG. 9).

Figure 10:
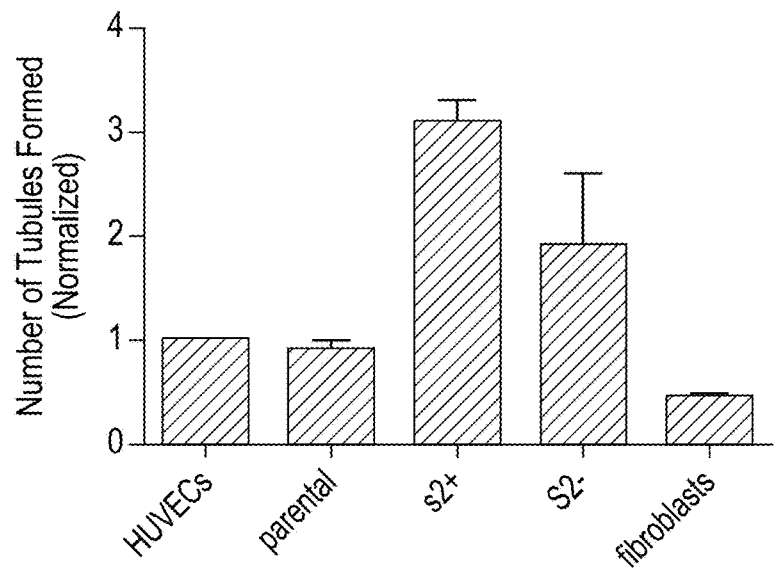
FIG. 10 shows relative HUVEC cord formation of SDC2+ and SDC2– stromal stem cells in response to in vitro angiogenic stimulation.

Human vascular endothelial cells (HUVEC) can form angiogenic cord-like tubules within 24 hours of being plated on nutrient-rich matrigel. Co-culture of SDC2+ SSC at a ratio of 1:1 with HUVEC on matrigel elicits a 3-fold increase in the number of stable vascular tubules at 24 hours (FIG. 10).

Figure 11:
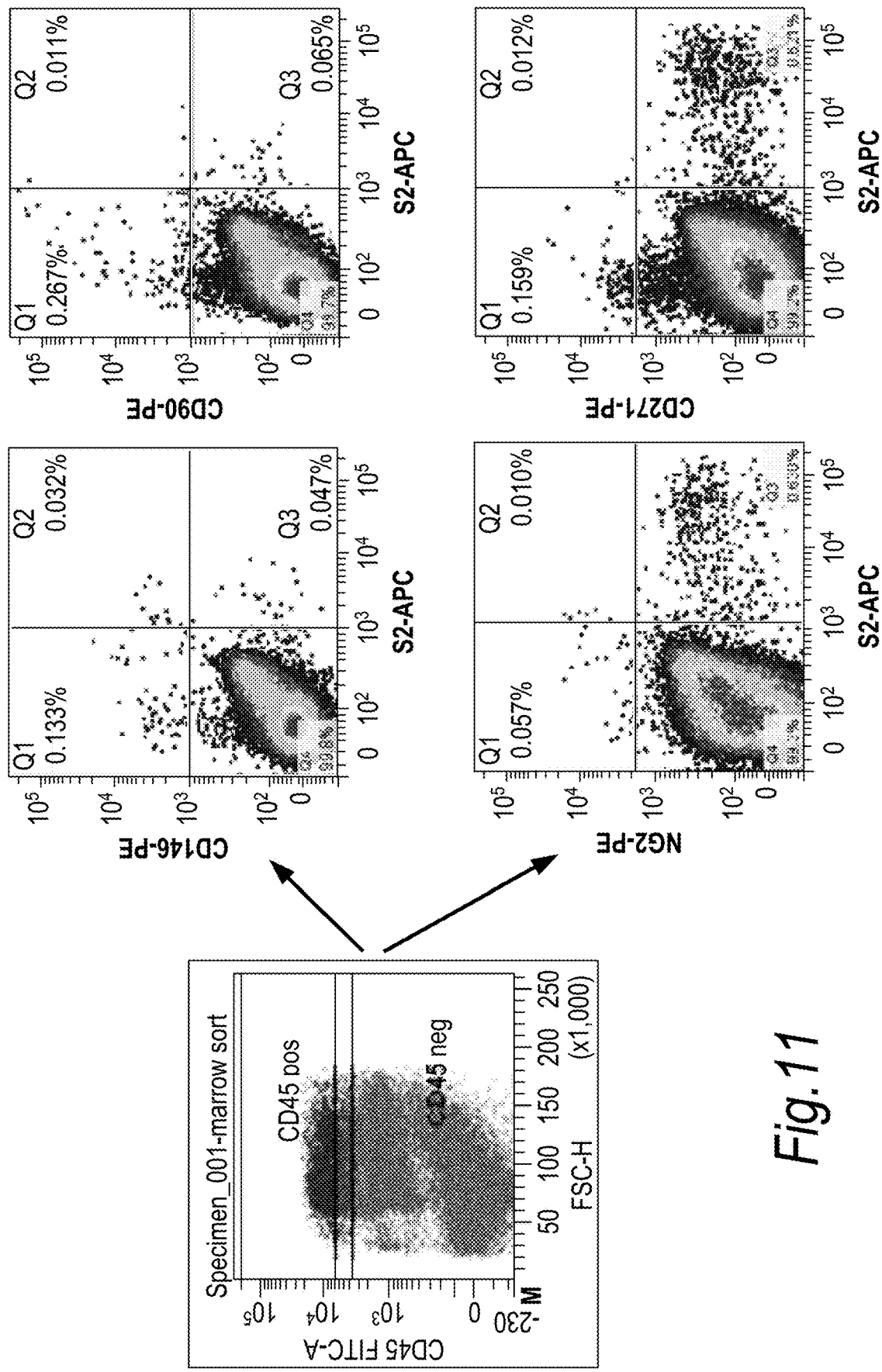
FIG. 11 shows that rare CD45–/SDC+ human bone marrow mononuclear cells express stromal stem cell marker CD271, CD146 and NG2.

Finally, Human SDC2+/CD45− MNC also express key stromal markers including CD146, NG2 (CSPG4) and CD271 (FIG. 11).

Figure 12:
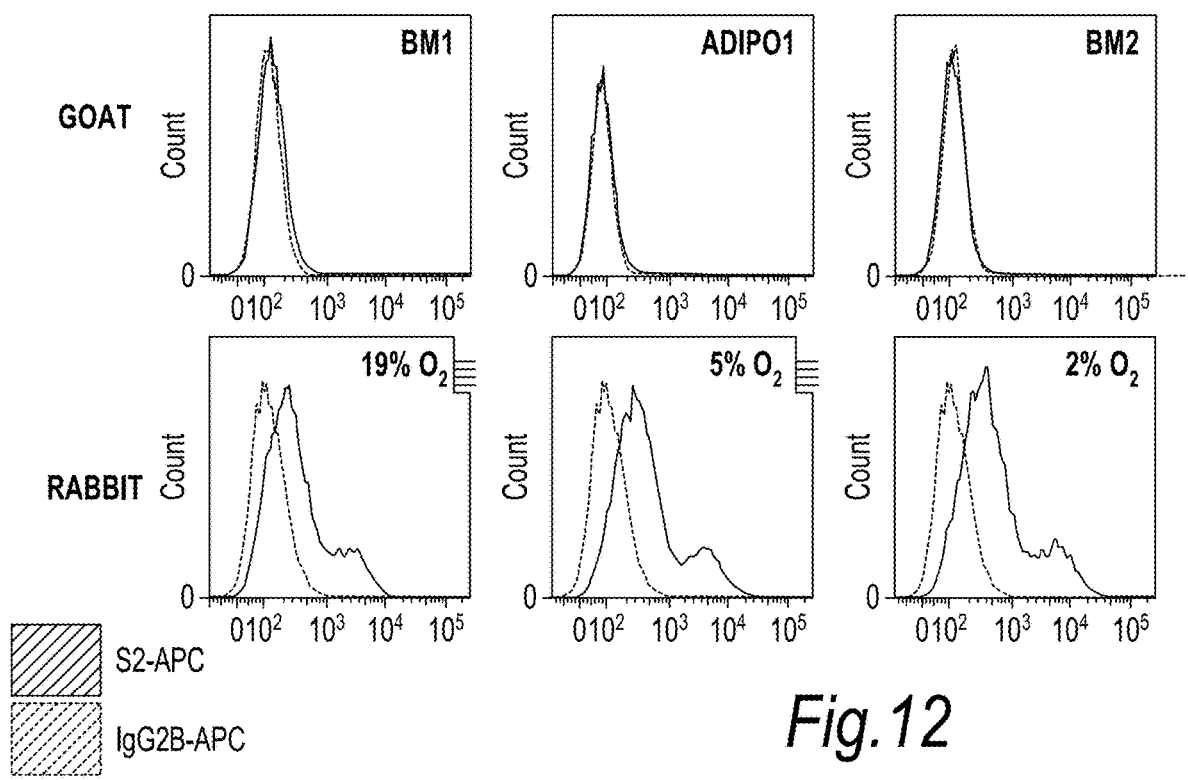
FIG. 12 shows SDC2 expression of stromal stem cells isolated from and rabbit bone marrow.

FIG. 12 represents flow cytometry histograms of SSC derived from BM and Adipose MNC of goat and rabbit BM tissue. While the SDC2 marker does not appear to be detectable on goat SSC, significant levels of SDC2 protein can be detected on rabbit SSC (FIG. 12).

Figure 13:
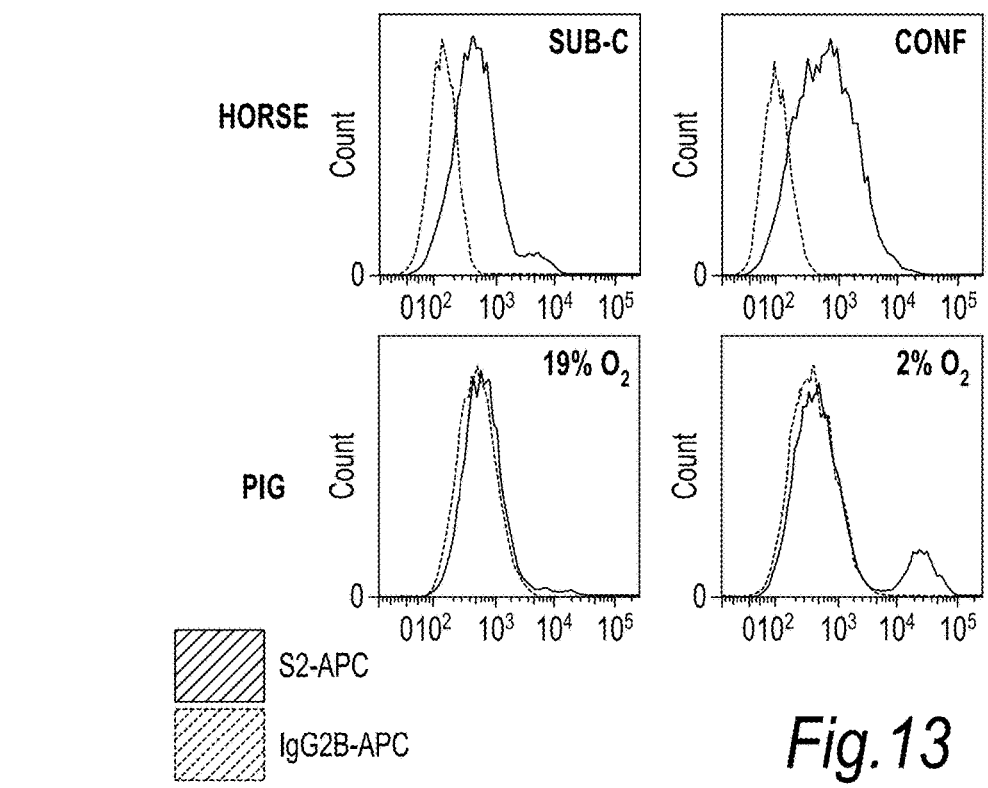
FIG. 13 shows increasing levels of SDC2 in stromal stem cells derived from equine bone marrow upon confluence, and stromal stem cells derived from pig bone marrow express SDC2 in low oxygen tension.

An increased detection of SDC2 protein is increased in cultured equine SSC in response to confluent culture (FIG. 13). SDC2 protein can also be detected in a sub-population of porcine SSC when cultured in low oxygen tension (FIG. 13).

Figure 14:
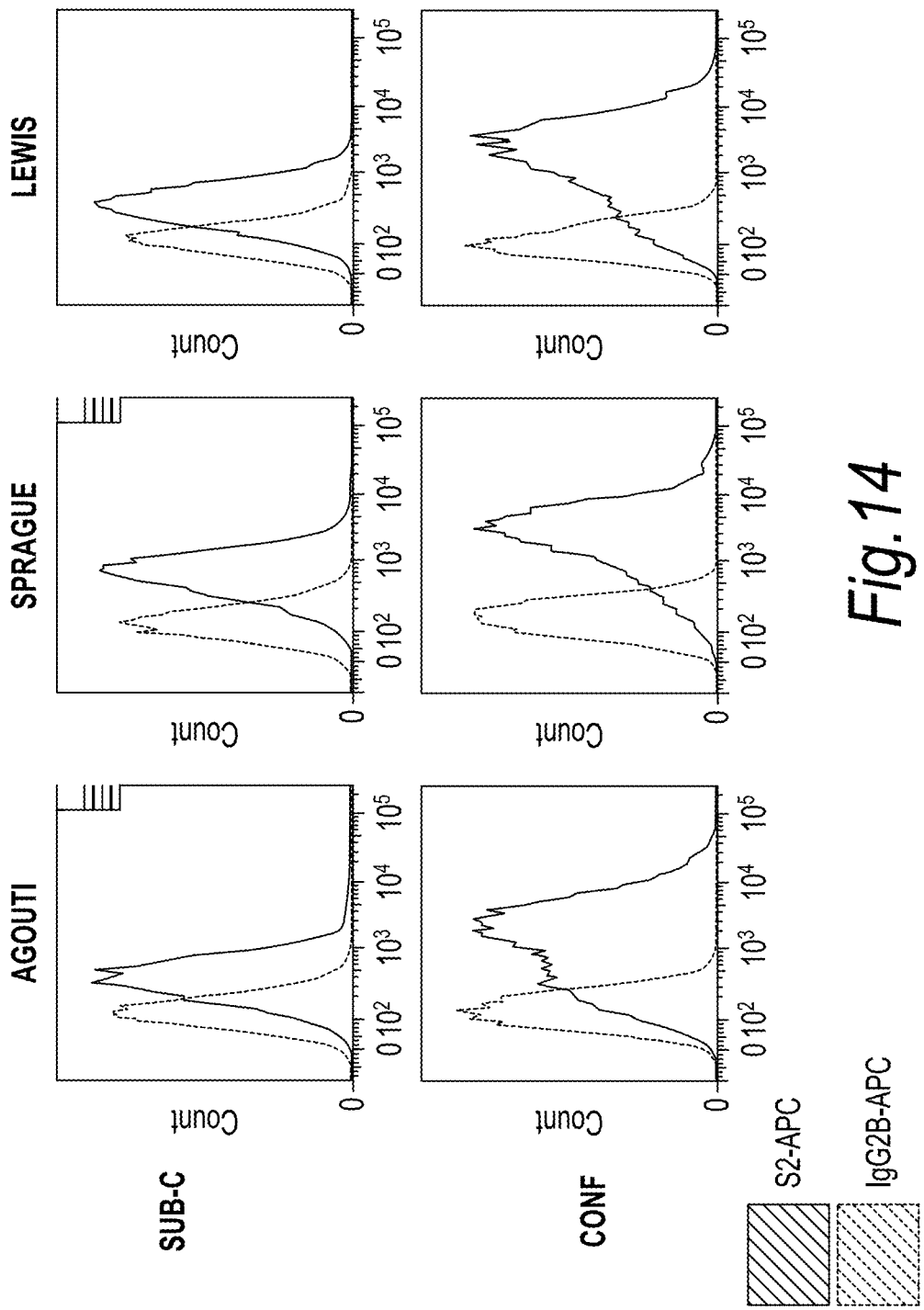
FIG. 14 shows increasing levels of SDC2 in stromal stem cells derived three strains of rat bone marrow upon confluence.
Figure 15:
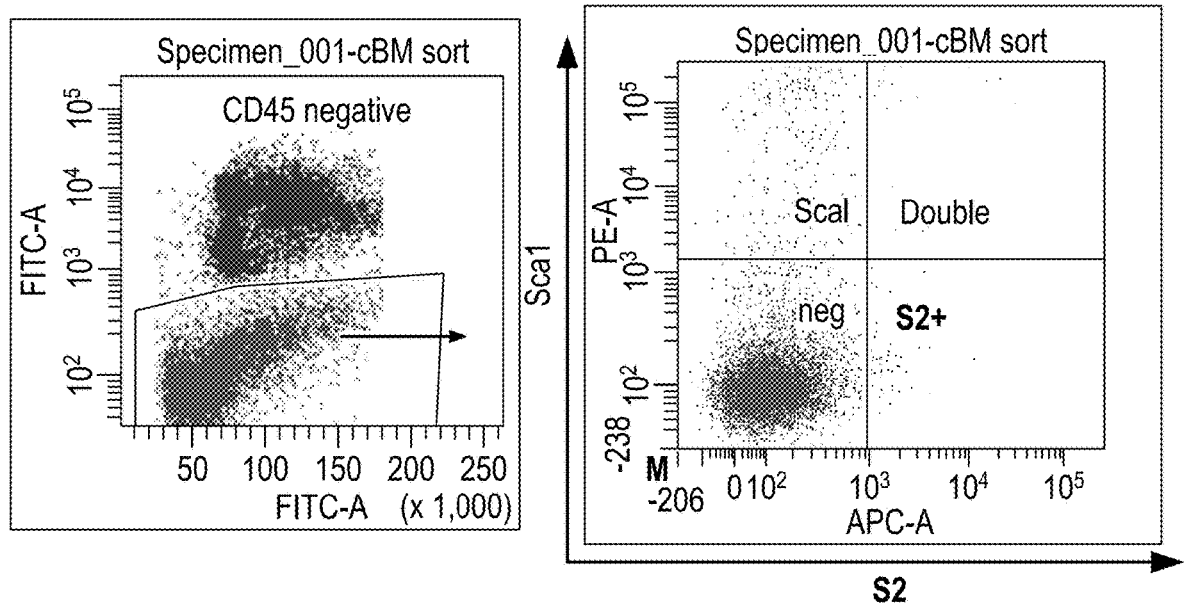
FIG. 15 shows FACS isolation of CD45– mononuclear cell with co-stain for SDC2 and Sca1.
Figure 16:
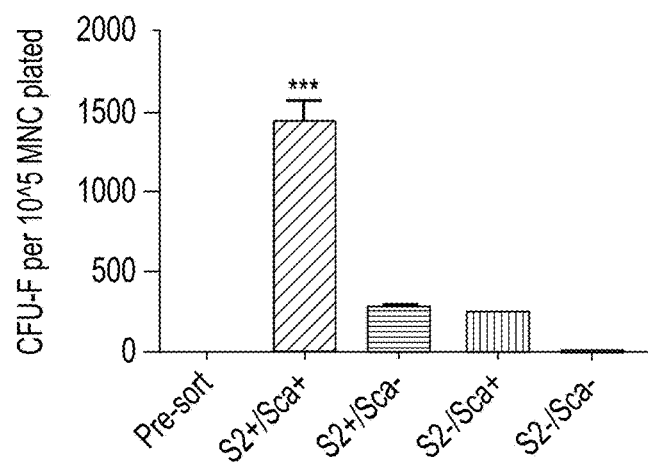
FIG. 16 shows enhanced enrichment in CFU-F in SDC+/Sca1 selected mouse mononuclear cells.

SDC2 marker is expressed on the surface of rat SSC (FIG. 14). As seen in equine SSC, SDC2 protein increases in the surface of rat SSC in response to confluence. This pattern can be seen in SSC derived from the marrow of three typically used laboratory strains of rat, namely, Dark Agouti, Sprague Dawley and Lewis (FIG. 14).

EXAMPLES

Example 1.1—Isolation of Bone Marrow Aspirates

Human bone marrow samples were obtained from the posterior iliac crest of healthy volunteers (n=3) following written consent from the patients. Patients underwent virology testing for HIV I and II, Hep A/C, HBsAg, Anti-HB core, Syphilis and CMV in accordance with EU Tissue Directive 2006/17/EC requirements. In a BSC, samples are pooled and divided into 7.5 mL aliquots and subjected to density-gradient centrifugation.

Example 1.2—Isolation and Expansion of Human SSC by Density-Gradient Centrifugation (Ficoll)

In a biological safety cabinet under aseptic techniques, 7.5 mL of Ficoll is pipetted into 50 ml centrifuge tubes. To remove clots, the 30 ml of BM was filtered through a 100 micron cell sieve (BD Falcon) into a 50 ml centrifuge tube. Filtered marrow was diluted 1/1 in D-PBS and then split evenly between the 4 tubes containing Ficoll, slowly pipetting the BM onto the side of the tube lying at an angle of 35° to 45° to insure a slow release of BM, without disturbing Ficoll or producing bubbles. Tubes were then centrifuges for 22 mins at 900 g with centrifuge brakes set to zero to form a fractionated sample. After centrifugation, tube contents formed three layers; a top layer of plasma, a thin layer—Buffy coat—contains the MNC, a clear layer of Ficoll and a bottom layer containing red blood cells constituents—erythrocytes and granulocytes. The Buffy coat was carefully aspirated out being careful not to disturb the surrounding cells. These cells were then transferred to another 50 mL centrifuge tube and resuspended in 45 mls D-PBS. These tubes were then centrifuged for 10 mins at 350 g. Supernatant was aspirated and pellets resuspended in 5 mL complete media. These were then centrifuged for 10 mins at 350 g. Supernatant was aspirated and pellets were pooled in 5 mL D-PBS.

Example 1.3—CFU-F Plates Seeding

After isolation of mononuclear cells via direct plating or Ficoll, $9 \times 10^6$ cells were isolated from both sets of cells and seeded in 10 cm dishes in triplicate at a seeding density of $3 \times 10^6$ MNC/plate. These cells were washed and fed at same time as cells in culture as outlined above.

Example 1.4—Crystal Violet CFU-F Staining

On days 12-14, cells were fixed and stained for CFU-F analysis. Media was aspirated from plates and plates were washed three times in D-PBS to remove and remaining media. Cells were fixed by pipetting 8 mL 95% Methanol, stored at −20° C., onto cells for 10 mins and gently swirling. Methanol was aspirated from plates and cells were washed once with D-PBS. 8 mL of crystal violet (0.5% crystal violet, 99.5% Methanol) was then added to plates and plates were gently swirled. Plates were left for 10-15 mins. Excess crystal violet was aspirated and cells were washed three times with D-PBS to remove and remaining excess stain. Plates were then inverted and left to dry overnight. Dry plates were then imaged using a flat bed scanner. Colonies were then counted and characterised by visual inspection under an inverted light microscope (Olympus CKx41). Colonies comprised of clusters greater than 50+ were counted as a CFU.

Example 2—Antibody Analysis of Mononuclear Cells and Stromal Stem Cells

Table 1 shows the details of the antibodies used to profile the mononuclear cells and stromal stem cells produced in Example 1.

TABLE 1

| Antibody | Supplier | Catalogue No. |
|---|---|---|
| CD362/Sydecan-2 | R&D Systems | N/A |
| CD271/LNGFR | BD | N/A |
| W8B2/TNAP/ALP | Miltenyi | N/A |
| TWEAK/TNFSF13 | BD | N/A |
| APRIL/CD256 | BD | N/A |
| CD146 | BD | N/A |
| CD105 | Invitrogen | MHCD10504 |
| CD73 | BD | 550257 |
| CD90 | BD | 555596 |
| CD14 | AbD Serotec | SFL2185 |
| CD19 | BD | 345777 |
| CD3 | BD | 345765 |
| CD34 | BD | 555822 |
| CD45 | BD | 555483 |
| Γ1, γ2a controls | BD | 342409 |
| HLA-DR | Invitrogen | MHLDR04 |
| Γ2b control | Caltag | MG2b04 |

Blocking Solution Preparation

Blocking solution was prepared by adding 1 mL of FBS to 49 mL of D-PBS in a 50 mL tube.

Sample Preparation

Cells were trypsinised at 37° C. and transferred to culture media in 15 mL tube. Cells were centrifuged for 5 mins at 400 g. Supernatant was aspirated and cells resuspended in 5 mL complete culture media. Cell counts and viability testing were performed using Trypan blue. Cells were then centrifuged for 5 mins at 400 g and supernatant aspirated. Blocking solution was then added to cell pellets to resuspend cells at 1×10⁶ cells/mL.

Staining of SSC (Analysis on FACS Canto)

PE-labelled antibodies were removed from refrigeration and placed on ice along with a 96 well round bottomed plate (Sarstedt) and blocking solution. 1×10⁵ cells (100 μL) was pipetted into each of 12 wells of the 96 well plate on ice, one for each antibody and 1 for unstained cells. Plate was then centrifuged for 4 mins at 400 g, 4° C. Supernatant was aspirated carefully to not disturb cell pellet and 50 μL of blocking solution was added to each well and pellet resuspended by pipetting of solution.

Example 3—Chondrogenic Differentiation of SSC

Table 2 shows the composition of the incomplete chondrogenic media (ICM).

TABLE 2

| Reagent | Volume | Final Concentration |
|---|---|---|
| DMEM (HG) | 95 mL | |
| Dexamethasone 1 mM | 10 μL | 100 nM |
| Ascorbic acid 2-P: 5 mg/mL | 1 mL | 50 μg/mL |
| L-Proline: 4 mg/mL | 1 mL | 40 μg/mL |
| ITS + supplement | 1 mL | 6.25 μg/mL bovine insulin |
| | | 6.25 μg/mL transferrin |
| | | 6.25 μg/mL selenous acid |
| | | 5.33 μg/mL linoleic acid |
| | | 1.25 mgmL BSA |
| Sodium pyruvate | 1 mL | 1 mM |
| Penicillin/Streptomycin | 1 mL | 100 U/mL penicillin |
| | | 100 μg/mL streptomycin |

Cells were thawed using 37° C. water bath and quickly transferred to culture media in 15 mL tube, washing out the cryovial with 1 mL of media. Cells were centrifuged for 5 mins at 400 g. Supernatant was aspirated and cells resuspended in 5 mL complete culture media. Cell count was performed and enough cells were harvested to form pellets of between 2-2.5×10⁵ cells/pellet. 4 positive cultures and 2 negative cultures were set up for each sample. Cells were centrifuged again for 5 mins at 400 g to remove culture media. Supernatant was aspirated and cells resuspended in 3 mL incomplete chondrogenic media (ICM). 3 mL cell suspension was divided into 15 mL tubes (2 mL for positive pellets, 1 mL for negative pellets). Tubes were centrifuged for 5 mins at 100 g. Cells for positive pellets were resuspended in 500 μL of complete chondrogenic media (CCM) for every pellet to be formed. CCM consists of ICM with 0.5 μL of TGF-β per mL of ICM.

Cells for negative pellet were resuspended in 500 μL of ICM for every pellet to be formed. Cells were transferred to screw cap Eppendorf tubes and centrifuged for 5 mins at 100 g in a swing out rotor. Tube caps loosened to allow gas exchange and incubated in BSC at 37° C., 5% $CO_2$. Media was changed every second day by aspirating as much of the media as possible without disturbing the pellet and replacing with either CCM or ICM for positive pellets and negative pellets respectively. At day 21, cell pellets were harvested by aspirating off all the media and washing twice in D-PBS. Pellets were allowed to air dry and 3 of the 4 positive pellets were used for GAG measurement and the other one was used for histology. Pellets for GAG measurement were stored at −20° C. and pellet used for histology was fixed in 10% formalin for 1 hr and then stored in water until ready to be processed.

Example 4—Chondrogenic Assay

Preparation of DMMB Stock Solution 16 mg of DMMB was dissolved overnight in 5 mL of reagent grade 100% ethanol. 2.73 g NaCl and 3.04 g Glycine was added to 975 mL of deionised water. 0.69 mL of conc HCI (11.6M) was added to this solution and mixed. Dissolved DMMB was added to this solution. Container of DMMB was then rinsed repeatedly with Dl water until all of DMMB solution was transferred. pH was adjusted to 3.0 with 1 M HCI. Volume was adjusted to 1 L with deionised water and solution was protected from light by wrapping in tinfoil.

Papain solution was prepared by dissolving 1 mg of papain (Sigma P4762) in 9.75 mL of warm diluted buffer. Diluted papain was prepared by adding 250 μL of this solution to 10 mL of dilution buffer.

200 μL of papain solution was added to each pellet and allowed to digest overnight in 60° C. oven. Samples were then vortexed to disperse pellet. Standards were made up using chondroitin-6-sulphate (Sigma C4384) by adding 4 mg of chondroitin-6-sulphate to 10 mL of dilution buffer making a 400 m/mL stock. This was then diluted to give a 40 μg/mL solution. Dilutions were made as follows from this 40 μg/mL solution as shown in table 3.

TABLE 3

| Chondroitin sulphate solution (40 μg/mL) | Dilution Buffer | Concentration GAG/well (50 μL) |
|---|---|---|
| 200 μL | 0 μL | 2 μg |
| 180 μL | 20 μL | 1.8 μg |
| 160 μL | 40 μL | 1.6 μg |
| 120 μL | 80 μL | 1.2 μg |
| 80 μL | 120 μL | 0.8 μg |
| 40 μL | 160 μL | 0.4 μg |
| 0 μL | 200 μL | 0 μg |

500 μL of standards and samples were added in triplicate to each well of a 96 well plate. 200 μL of DMMB stock solution was added to each well and incubated at room temperature (RT) for 5 mins. Plates were read using an absorbance plate reader at 595 nm. Absorbance readings for standards containing 0 μL GAG/well where used as a blank value and subtracted from other absorbance readings.

Measurement of DNA Using PicoGreen

1×TE solution was prepared by diluting the 20× stock solution provided in the Quant-iT Kit (Sigma P75 89) 1 in 20 parts in distilled water. A diluted PicoGreen solution was prepared by diluting DMSO to 1 in 200 parts $dH_2O$. DNA stock (100 g/mL) was diluted in 1×TE 50-fold to give a final concentration of 2 g/mL DNA standards were prepared as shown in table 4.

TABLE 4

| DNA Working Stock | 1 × TE | Final conc DNA/mL |
|---|---|---|
| 400 μL | 0 | 2000 ng |
| 200 μL | 200 μL | 1000 ng |
| 100 μL | 300 μL | 500 ng |
| 40 μL | 360 μL | 200 ng |
| 20 μL | 380 μL | 100 ng |
| 10 μL | 390 μL | 50 ng |
| 4 μL | 396 μL | 10 ng |
| 0 μL | 400 μL | 0 ng |

Papain-digested samples (outlined above) were further diluted 25-fold in 1×TE. 100 μL of standards and samples were added in triplicate to a 96-well black plate. Plate must be black as reaction is affected by light. 100 μL of PicoGreen solution was added to each standard and sample well and allowed to incubate for 2-3 mins. Plates read on fluorescent plate reader by first exciting plate at 485 nm and then reading plate at 538 nm.

Example 5—Adipogenic Differentiation of SSC

Table 5 shows the composition of the adipogenic induction media.

TABLE 5

| Reagent | Volume (to make 100 mL) | Final Concentration |
|---|---|---|
| DMEM (HG) | 87.6 mL | |
| Dexamethasone 1 mM | 100 μL | 1 μM |
| Insulin 1 mg/mL | 1 mL | 10 μg/mL |
| Indomethacin 100 mM | 200 μL | 200 μM |
| 500 mM MIX | 100 μL | 500 μM |
| Penicillin/Streptomycin | 1 mL | 100 U/mL penicillin 100 μg/mL streptomycin |
| FBS | 10 mL | 10% |

Table 6 shows the composition of the adipogenic maintenance media.

TABLE 6

| Reagent | Volume (to make 100 mL) | Final Concentration |
|---|---|---|
| DMEM (HG) | 88 mL | |
| Insulin 1 mg/mL | 1 mL | 10 μg/mL |
| Penicillin/Streptomycin | 1 mL | 100 U/mL penicillin 100 μg/mL streptomycin |
| FBS | 10 mL | 10% |

Cells were thawed using 37° C. water bath and quickly transferred to culture media in 15 mL tube, washing out the cryovial with 1 mL of media. Cells were centrifuged for 5 mins at 400 g. Supernatant was aspirated and cells resuspended in 5 mL complete culture media. Cell count was performed and enough cells were harvested to seed cells at confluency ($4 \times 10^4$ cells/well) in a 24 well plate with flat bottom. 4 test wells and 4 control wells were setup. Cells were seeded in 1 mL of culture media in each well. Cells were incubated at 37° C., 5% $CO_2$ and after 48 hrs cells were viewed to have adhered to the plastic and appeared confluent. To test wells, complete culture media was replaced with 1 mL of adipogenic induction media and left for 3 days. Control wells were replaced with complete culture media. After 3 days in adipogenic culture media, media in test wells was replaced with 1 mL/well of maintenance media and left for between 1 and 3 days. This was then replaced with 1 mL/well of maintenance media. This process was repeated three times. After the final media change to maintenance media, cells were left in media for 5 to 7 days before harvesting.

Example 6—Adipogenic Assay Oil Red O Staining

A working solution of Oil Red O was prepared by mixing 6 parts of Oil Red O stock solution with 4 parts of $dH_2O$. Solution was allowed to stand for 10 mins and then filtered through Whatman no. 1 Filter paper.

Media was aspirated and cells washed twice in D-PBS. Cells were then fixed in 10% formalin for 1 hr at RT. Formalin was aspirated and plates rinsed in $dH_2O$. 500 μL of Oil Red O working solution was pipetted to each well to cover layer of cells. Plate rotated slowly in FIG. 8 motion to spread Oil Red O over cells evenly and left for 5 mins. Stain was aspirated and excess stain was removed by adding 2 mL/well of 60% Isopropanol. Plates were again swirled in FIG. 8 motion and Isopropanol aspirated. Plates rinsed with tap water until water ran off plate smoothly. Samples were then stored in $dH_2O$ until imaging.

Extraction of Stained Lipid

After imaging of samples, water was aspirated from wells. Oil Red O was extracted by pipetting Isopropanol (2×500 μL) over the surface of the wells several times. Isopropanol and dye were then transferred to an Eppendorf tube. Samples were centrifuged for 2 mins at 500 g to pellet and debris in samples. 200 μL of the extracted stain for each sample was added in triplicate to a 96 well plate. Staining was measured using a plate reader at 520 nm.

Example 7—Osteogenic Differentiation of SSC

Table 7 shows the composition of the osteogenic differentiation media.

TABLE 7

| Reagent | Volume (to make 100 mL) | Final Concentration |
|---|---|---|
| DMEM (LG) | 87.5 mL | |
| Dexamethasone 1 mM | 10 μL | 100 nM |
| Ascorbic acid 2-P 10 mM | 1 mL | 100 μM |
| B glycerophosphate | 1 mL | 10 mM |
| FBS | 10 mL | 10% |
| Penicillin/Streptomycin | 1 mL | 100 U/mL penicillin 100 μg/mL streptomycin |

Cells were thawed using 37° C. water bath and quickly transferred to culture media in 15 mL tube, washing out the cryovial with 1 mL of media. Cells were centrifuged for 5 mins at 400 g. Supernatant was aspirated and cells resuspended in 5 mL complete culture media. Cell count was performed and enough cells were harvested to seed cells at confluency ($4 \times 10^4$ cells/well) in a 24 well plate with flat bottom. 4 test wells and 4 control wells were setup. Cells were seeded in 1 mL of culture media in each well. Cells were incubated at 37° C., 5% $CO_2$ and after 48 hrs cells were viewed to have adhered to the plastic and appeared confluent. Media in test wells was replaced with osteogenic media and media in control wells was replaced with complete culture media. Media in all wells was changed twice weekly. Cells were harvested between days 10 and 17.

Osteogenic Assay 1 of 4 test wells and control wells are used for Alizarin Red staining. The other 3 were used for calcium quantification.

Alizarin Red Staining

2% Alizarin Red S solution was prepared by dissolving 2 g Alizarin Red S in 100 mL $dH_2O$. Solution was mixed and pH was adjusted to approximately 4.1-4.3 using 1% ammonium hydroxide as pH is essential for staining process. Media was aspirated from wells. Cells were washed twice in D-PBS to remove remaining media to insure no staining of media occurred. 95% methanol was prepared by diluting 95 mL 100% methanol with 5 mL water. Methanol was then stored in ice to low temperature. Cells were fixed in ice cold Methanol for 10 mins. Methanol was aspirated and cells were rinsed in $dH_2O$. 5000_, of 2% Alizarin Red S was added to wells and left for 5 mins, occasionally gently swirling the plate in FIG. 8 motion. After 5 mins calcium staining was visible. Cells rinsed in $dH_2O$ and imaged using an Olympus CKx41.

Calcium Assay 0.5M HCI was prepared by diluting 4.3 mL 11.6M HCI in 95.7 mL water. Media was aspirated from wells and wells washed twice in D-PBS to remove any remaining media. 0.2 mL 0.5M HCI was added to each well and cells were scraped from wells using a cell scraper and collected in labelled Eppendorf tubes. Solution was left shaking overnight on cell shaker in a dark cold room. Samples centrifuged briefly to pellet cell debris. Calcium assay was performed using a Stanbio Kit. A working solution of 1:1 of binding reagent and working dye were prepared.

Table 8 shows the composition of calcium assay standards.

TABLE 8

| Concentration (µg/well) | Volume 10 mg/dl std/well |
|---|---|
| 0 | 0 |
| 0.05 | 0.5 µL |
| 0.10 | 1 µL |
| 0.2 | 2 µL |
| 0.4 | 4 µL |
| 0.6 | 6 µL |
| 0.8 | 8 µL |
| 1.0 | 10 µL |

Standards and samples were plated in triplicate in a 96 well plate. 10 µL of 0.5M HCI was added to each standard well. 10 µL of samples were added to each well. 200 µL of working solution was added to every standard and sample well. Absorbance was read at 550-650 nm using a Victor3™ 1420.

SDC2 co-stained with Sca1 on the surface on CD45-ve murine BMMNC from the C57/BI6 strain. Moreover, FACS sorting of SDC2+/Sca1+ MNC from murine marrow reveals that SDC2 marks a self-renewing sub-population of SSC that can form CFU-F at significantly increased frequencies compared to plated pre-sorted MNC.

Example 8—SDC2+ Cells from Human Pluripotent Cells

We obtained populations of cells expressing SDC2 from human pluripotent cells, in this case ES cells (ES–), for comparison with cells derived from bone marrow (BM–).

BM-SSCs and ES-SSCs (Millipore Human Mesenchymal Stem Cells (derived from hES cells)) were plated at a density of $10^5$ cells per well of a 6-well plate (Nunc) in complete media (BM-SSCs: α-MEM, 10% FBS; ES-SSCs: Millipore FibroGRO™ LS Complete Media Kit) and left to adhere overnight. Cells were harvested when they reached subconfluent levels (~60% confluent), and confluent levels (100% confluent).

The results from flow cytometric analysis of "classical" SSC markers illustrated that BM-SSCs and ES-SSCs had similar expression of CD73. The expression of the marker CD105 remained the same for both confluent and sub-confluent cultures; CD105 expression appeared to decrease with increasing confluency. The expression of SDC2 by BM- and ES-SSCs remained consistent in confluent and sub-confluent culture conditions; the percentage population BM-SSCs expressing SDC2 increases in confluent culture and is consistently high for ES-SSCs in both confluent and nonconfluent cultures. The RFI of SDC2 expression by ES-SSC is higher.

Hence, hES derived stromal stem cells expressed SDC2 and therefore cell populations enriched for SDC2 can be obtained direct from human pluripotent cells including hES and hiPS cells.

Example 9—SDC2* Cells in Treatment of Ventilator Induced Lung Injury in Rats Methods and Materials All work was approved by the Animal Ethics Committee of the National University of Ireland, Galway and conducted under license from the Department of Health, Ireland.

hSSC Isolation and Culture

Human SSCs (hSSCs) were isolated from adult volunteers as previously described. Following aspiration, the bone marrow was plated into tissue culture flasks. Adherent cells were grown until 80% confluent and then trypsinized and culture expanded to passage 4, whereupon they were used for experiments. SSCs were characterized according to international guidelines. Fibroblasts, used as control cells, were obtained from a stable cell line as previously described.

Series 1 [Ventilation Induced Lung Injury]

Adult male Sprague Dawley rats were anesthetised, orotracheally intubated and randomized to undergo injurious mechanical ventilation.

The following ventilator settings were used: $P_{Insp}$ 35 $cmH_2O$, respiratory rate 18 $min^{-1}$, and PEEP 0 $cmH_2O$. When respiratory static compliance had decreased by 50% the animals were allowed to recover.

Following recovery, animals were randomized to intravenous administration of: (i) vehicle (PBS, 300 µL); (ii) fibroblasts ($4 \times 10^6$ cells); (iii) human SSCs ($4 \times 10^6$ cells) or (iv) cells of the invention, referred to as human S2+SSCs ($4 \times 10^6$ cells); in a four group design.

The extent of recovery following ALI and the inflammatory response was assessed after 24 hours.

Series 2 [Low Stretch 'Protective Ventilation]

Adult male Sprague Dawley rats were anesthetised, orotracheally intubated and randomized to low stretch mechanical ventilation.

The 'low stretch' protocol comprised of mechanical ventilation for 90 minutes with the following settings: $FiO_2$ of 0.3, respiratory rate 80.$min^{-1}$, tidal volume 6 ml·$kg^{-1}$ and positive end-expiratory pressure of 2 cm $H_2O$ Following recovery, animals were randomized to intravenous administration of: (i) vehicle (PBS, 300 µL); (ii) fibroblasts ($4 \times 10^6$ cells); or (iii) intra-tracheal human SSCs ($4 \times 10^6$ cells); in a six group design.

The extent of recovery following ALI and the inflammatory response was assessed after 24 hours.

Statistical Analysis

The distribution of all data was tested for normality using Kolmogorov-Smirnov tests. Data were analyzed by one-way ANOVA, followed by Student-Newman-Keuls, or by Kruskalis-Wallis followed by Mann-Whitney U test with the Bonferroni correction for multiple comparisons, as appropriate. Underlying model assumptions were deemed appropriate on the basis of suitable residual plots. A two-tailed p value of <0.05 was considered significant.

Results

Efficacy of S2+SSCs in Enhancing Recovery from Ventilation Induced ALI 40 animals were entered into the experimental protocol, with 10 allocated to each of the VILI groups. Four VILI animals, two allocated to receive vehicle, and two allocated to receive fibroblasts, did not survive the injury protocol. All other animals survived the injury protocol and subsequent treatment allocation. 8 animals each were entered into the vehicle control and fibroblast groups, while 10 animals each received hSSCs and S2+SSCs.

Baseline Characteristics: There were no differences among the VILI groups at baseline in terms of pre-injury variables, the duration of injurious ventilation or the extent of the lung injury produced (Table 9).

TABLE 9

Baseline data regarding animals subjected to high stretch Ventilation.

| | High Stretch Ventilation | | | |
|---|---|---|---|---|
| Variable | Vehicle | Fibroblasts | hSSCs | S2+SSCs |
| Number of animals | 8 | 8 | 10 | 10 |
| Animal Weight (g) | 400 ± 26 | 392 ± 51 | 410 ± 19 | 417 ± 18 |
| Ventilation Time (mins) | 76 ± 27 | 76 ± 16 | 77 ± 19 | 78 ± 14 |
| Lung compliance Pre-injury (ml/mmHg) | 0.64 ± 0.09 | 0.66 ± 0.12 | 0.67 ± 0.13 | 0.66 ± 0.11 |
| Lung compliance post-VILI | 0.31 ± 0.02 | 0.32 ± 0.02 | 0.31 ± 0.03 | 0.32 ± 0.03 |

Note:
Data are expressed as mean ± SD.

S2+SSCs restored lung function and structure following VILI: S2+SSC therapy enhanced restoration of arterial oxygenation, as evidenced by a reduced alveolar-arterial oxygen gradient compared to vehicle ($p<0.05$). Further functional recovery in lung physiology in response to S2+SSC therapy was demonstrated by significant improvements ($p<0.01$) in respiratory system static compliance in comparison to vehicle.

S2+SSCs improved lung microvascular permeability, as evidenced by a decrease in lung wet:dry weight ratios and a decrease in alveolar fluid protein concentrations (Table 10). hSSCs enhanced recovery of lung structure. S2+SSCs decreased alveolar thickening, as evidenced by reduced alveolar tissue volume fraction, and increased recovery of airspace volume, as evidenced by increased alveolar airspace volume fraction (Table 10).

TABLE 10

Data regarding extent of resolution 24 hours following high stretch Ventilation.

| | High Stretch Ventilation | | | |
|---|---|---|---|---|
| Variable | Vehicle | Fibroblasts | hSSCs | S2+SSCs |
| Arterial O2 tension (FiO2 = 0.3; KPa) | 13.4 ± 2.8 | 12.7 ± 2.8 | 16.9 ± 2.9* | 17.0 ± 1.7* |
| Arterial O2 tension (FiO2 = 1.0; KPa) | 32.1 ± 13.1 | 32.8 ± 16.0 | 65.3 ± 9.4* | 56.2 ± 14.4* |
| Lung Static Compliance (ml/mmHg) | 0.37 ± 0.04 | 0.34 ± 0.08 | 0.55 ± 0.14* | 0.53 ± 0.08* |
| Lung Wet:Dry weight ratios | 5.9 ± 0.8 | 5.4 ± 0.9 | 4.6 ± 0.2* | 4.3 ± 0.7* |

Note:
Data are expressed as mean ± SD. Final data is data collected upon completion of the experimental protocol.
*Significantly different vehicle and fibroblast groups.

S2+SSCs modulated inflammation following VILI: S2+SSCs decreased total inflammatory cell counts in BAL (bronchoalveolar lavage) fluid and substantially attenuated ($p<0.001$) lung neutrophil accumulation. Both S2+SSCs and undifferentiated hSSCs were equally effective in modulating the inflammatory response following VILI (Table 11).

TABLE 11

Data regarding the inflammatory response 24 hours following high stretch Ventilation.

| | High Stretch Ventilation | | | |
|---|---|---|---|---|
| Variable | Vehicle | Fibroblasts | hSSCs | S2+SSCs |
| BAL Cell Counts ($\times 10^5$/ml) | 2.91 ± 1.0 | 3.42 ± 0.86 | 1.30 ± 0.32* | 1.50 ± 0.51* |
| % BAL Neutrophils (%) | 44.7 ± 12.2 | 56.7 ± 3.4 | 15.8 ± 8.5* | 16.0 ± 8.5* |
| BAL Neutrophil Counts ($\times 10^5$/ml) | 1.31 ± 0.60 | 1.92 ± 0.44 | 0.20 ± 0.10* | 0.27 ± 0.22* |
| BAL Lymphocyte Counts ($\times 10^5$/ml) | 1.57 ± 1.02 | 0.94 ± 0.44 | 0.57 ± 0.14† | 1.03 ± 0.67 |

Note:
Data are expressed as mean ± SD. Final data is data collected upon completion of the experimental protocol.
*Significantly different vehicle and fibroblast groups.
†Significantly different from vehicle Group Effect on 'non-injury' parameters: There was no effect of S2+SSCs or undifferentiated hSSCs on arterial pH, $PCO_2$, bicarbonate, base excess, lactate or mean arterial pressure (data not shown).

Effect of S2+SSCs in Animals Following Low Stretch Ventilation 16 animals were entered into the experimental protocol, with 4 allocated to each of the groups. All animals survived the injury protocol and subsequent treatment allocation.

Baseline Characteristics: There were no differences among the protective ventilation groups at baseline in terms of pre-injury variables, the duration of injurious ventilation or the extent of the lung injury produced (data not shown).

S2+SSCs did not affect lung function or structure: There was no effect of S2+SSC therapy on lung structure or function following protective ventilation (Table 12).

TABLE 12

Data regarding extent of resolution 24 hours following low stretch Ventilation.

| | Low Stretch Ventilation | | | |
|---|---|---|---|---|
| Variable | Vehicle | Fibroblasts | hSSCs | S2+SSCs |
| Arterial O$_2$ tension (FiO$_2$ = 0.3; KPa) | 17.6 ± 1.2 | 17.8 ± 0.8 | 17.8 ± 0.6 | 18.5 ± 0.7 |
| Arterial O$_2$ tension (FiO$_2$ = 1.0; KPa) | 65.8 ± 1.7 | 69.2 ± 1.7 | 68.8 ± 3.3 | 64.3 ± 6.3 |
| Lung Static Compliance (ml/mmHg) | 0.53 ± 0.03 | 0.59 ± 0.06 | 0.64 ± 0.02 | 0.61 ± 0.04 |
| Lung Wet:Dry weight ratios | 4.3 ± 0.4 | 4.3 ± 0.5 | 4.2 ± 0.2 | 4.3 ± 0.6 |

Note:
Data are expressed as mean ± SD. Final data is data collected upon completion of the experimental protocol.

S2+SSCs did not cause inflammation: There was no effect of S2+SSCs therapy on the inflammatory response in the lung structure following protective ventilation (Table 13).

TABLE 13

Data regarding the inflammatory response 24 hours following low stretch Ventilation.

| | Low Stretch Ventilation | | | |
|---|---|---|---|---|
| Variable | Vehicle | Fibroblasts | hSSCs | S2+SSCs |
| BAL Cell Counts (×10$^5$/ml) | 1.24 ± 0.24 | 1.08 ± 0.13 | 1.01 ± 0.10 | 1.14 ± 0.32 |
| % BAL Neutrophils (%) | 11.3 ± 2.8 | 9.8 ± 2.1 | 20.8 ± 4.9 | 10.3 ± 2.0 |
| BAL Neutrophil Counts (×10$^5$/ml) | 0.14 ± 0.06 | 0.10 ± 0.02 | 0.21 ± 0.04 | 0.11 ± 0.03 |
| BAL Lymphocyte Counts (×10$^5$/ml) | 0.64 ± 0.16 | 0.65 ± 0.38 | 0.65 ± 0.52 | 0.59 ± 0.31 |

Note:
Data are expressed as mean ± SD. Final data is data collected upon completion of the experimental protocol.

Effect on 'non-injury' parameters: There was no effect of S2+SSCs or undifferentiated hSSCs on arterial pH, PCO$_2$, bicarbonate, base excess, lactate or mean arterial pressure (Table 14).

TABLE 14

Data regarding 'non-injury' parameters 24 hours following low stretch Ventilation.

| | Low Stretch Ventilation | | | |
|---|---|---|---|---|
| Variable | Vehicle | Fibroblasts | hSSCs | S2+SSCs |
| Arterial pH | 7.40 ± 0.04 | 7.39 ± 0.03 | 7.38 ± 0.03 | 7.40 ± 0.04 |
| Arterial PCO$_2$ (KPa) | 5.4 ± 0.8 | 5.5 ± 0.2 | 5.0 ± 0.2 | 4.4 ± 0.3 |
| Arterial Bi-carbonate (mMol/L) | 20.5 ± 2.0 | 22.0 ± 1.5 | 20.9 ± 1.0 | 21.7 ± 2.1 |
| Base Excess | 3.4 ± 1.5 | 3.3 ± 1.7 | 3.4 ± 2.0 | 2.8 ± 1.8 |
| Arterial Lactate (mMol/L) | 3.1 ± 1.4 | 2.2 ± 0.6 | 2.1 ± 0.8 | 2.0 ± 1.2 |
| Mean Arterial Pressure (mmHg) | 113.2 ± 2.7 | 101.0 ± 10.7 | 98.0 ± 13.7 | 99.5 ± 17.1 |

Note:
Data are expressed as mean ± SD. Final data is data collected upon completion of the experimental protocol.

CONCLUSIONS

S2+SSCs of the invention restored lung function and structure following VILI, as evidenced by a reduced alveolar-arterial oxygen gradient, significant improvements (p<0.01) in respiratory system static compliance, and improved lung microvascular permeability. Also, they enhanced recovery of lung structure following VILI. The cells modulated inflammation following VILI, decreasing total inflammatory cell counts in BAL fluid and substantially attenuating (p<0.001) lung neutrophil accumulation. There was no effect of S2+SSC therapy on lung structure or function, or on the inflammatory response, following protective ventilation. These findings suggest that the cells of the invention are well tolerated in this model.

The invention thus provides methods of obtaining defined stromal stem cell populations and uses thereof.

The invention claimed is:

1. A method of treating an autoimmune disease in an individual, comprising administering to the individual a population of mammalian stromal stem cells, wherein 30% or more of the cells are positive for SDC2.

2. The method of claim 1, wherein the autoimmune disease is autoimmune hepatitis; primary biliary cirrhosis (PBC); primary sclerosing cholangitis (PSC); rheumatoid arthritis; autoimmune nephritis; Wegener's granulomatosis (WG); type 1 diabetes; type 2 diabetes; uveitis; autoimmune gastritis (AIG); multiple sclerosis; inflammatory bowel diseases; Crohn's Disease; Ulcerative colitis; fistulising Crohn's disease; scleroderma; lupus (SLE); Graves' Disease; autoimmune lymphoproliferative disease (ALPS); or laminitis.

3. The method of claim 1, wherein the individual is a mammal.

4. The method of claim 1, wherein the individual is a human.

5. The method of claim 1, wherein the method comprises administering the cells in a composition of the cells suspended in a liquid medium for injection.

6. The method of claim 5, wherein the composition is administered intravenously.

7. The method of claim 1, wherein the method comprises administering the cells in a composition of the cells suspended in a matrix.

8. The method of claim 7, wherein the composition is administered directly to a diseased tissue.

9. The method of claim 1, wherein the method comprises administering the cells in a pharmaceutically acceptable carrier.

10. The method of claim 9, wherein the pharmaceutically acceptable carrier is selected from the group consisting of saline, phosphate buffered saline, dimethylsulfoxide, collagen, hyaluronic acid, and human serum albumin.

11. The method of claim 1, wherein the method comprises administering at least $10^6$ cells.

* * * * *